United States Patent
Yeung

[11] Patent Number: 5,869,245
[45] Date of Patent: Feb. 9, 1999

[54] MISMATCH ENDONUCLEASE AND ITS USE IN IDENTIFYING MUTATIONS IN TARGETED POLYNUCLEOTIDE STRANDS

[75] Inventor: Anthony T. Yeung, Havertown, Pa.

[73] Assignee: Fox Chase Cancer Center, Philadelphia, Pa.

[21] Appl. No.: 658,322

[22] Filed: Jun. 5, 1996

[51] Int. Cl.$^6$ .............................. C12Q 1/68; C12N 19/16; C12N 19/14
[52] U.S. Cl. .............................. 435/6; 435/196; 435/195; 435/91.2
[58] Field of Search .............................. 435/6, 91.2, 183, 435/195, 196; 530/350

[56] References Cited

U.S. PATENT DOCUMENTS 5,459,039 10/1995 Modrich et al. .............................. 435/6
5,571,676 11/1996 Shuber ........................................ 435/6

FOREIGN PATENT DOCUMENTS

WO9302216 7/1992 WIPO.
WO9320233 10/1993 WIPO.
WO9529251 11/1995 WIPO .............................. C12P 19/34

OTHER PUBLICATIONS

Modrich, P., 1994 Science 266, 1959–1960.
Su, et al., 1988 J. Biol. Chem. 263, 5057–5061.
Finkelstein, E., et al. 1994 International Journal of Dermatology 33, 116–118.
Smith, P.K., et al. 1985 Analytical Chemistry 150, 76–85.
Jay et al. 1990 Analytical Biochem. 185, 324–330.
Yeung, A.T., et al., 1983 Proc. Nat. Acad Sci. USA, 80, 6157–6161.
Yeung, A.T., et al., 1988 Nucleic Acids Res, 16, 4539–4554.
Lyamichev, V., et al., 1993 Science 260, 778–783.
Ramotar, D., et al., 1987 J. Biol. Chem 262, 425–31.
Chow, T.Y.K., et al., 1987 J. Biol. Chem 262, 17659–17667.
Wyen, N.V., et al., 1971 Biochem Biophys Acta. 232, 472–483.
Brown, P.H., et al., 1987 Eur. J. Biochem 168, 357–364.
Hanson, D.M., et al., 1969 J. Biol. Chem. 244, 2440–2449.
Holloman, W.K., et al., 1981 J. Biol. Chem. 256, 5087–5094.
Badman, R., 1972 Genetic Res., Camb. 20, 213–229.
Shenk, T.E., et al., 1975 Proc. Nat. Acad. Sci. USA, 72, 989–993.
Maekawa, K., et al., 1991 Eur. J. Biochem 200, 651–661.
Kowalski, D., et al, 1976 Biochemistry 15, 4457–4462.
Kroeker, W.D., et al., 1976 Biochemistry 15, 4463–4467.
Ardelt, W., et al., 1971 Biochem. Biophys. Res. Commun. 44, 1205–1211.
Kowalski, D., 1984 Nucleic Acids. Res. 12, 7071–7086.
Strickland, J.A., et al., 1991 Biochemistry 30, 9749–9756.
Doetsch, P.W., et al., 1988 Nucleic Acids Res. 16, 6935–6952.
Caron, P.R., et al., 1985 Proc. Nat. Acad. Sci. USA 82, 4925–4929.
Yeh, Y.–C., et al., 1994 J. Biol. Chem. 269, 15498–15504.
Welch, W.J., et al., 1983 J. Biol. Chem. 258, 7102–7111.
Jackson, S.P., et al., 1989 Proc. Nat. Acad. Sci. USA 86, 1781–1785.
Jackson, S.P., et al., 1988 Cell 55, 125–133.
He, J., et al., 1995 Nature 373, 721–724.
Peeples, M.E. 1988 Virology 162, 255–259.
Buckley, A., et al., 1988 J. Gen. Virology, 69, 1913–1920.
Dodgson et al. (1977) Biochemisty 16:2374–79.
Youil et al. (1996) Genomics 32:431–35.
Gauffre, A., et al., 1992 Molecular Immunology 29, 1113–1120.
Jones, B.K., et al., 1988 Proc. Natl. Acad. Sci. USA 85, 8410–8414.
Sarker, et al., 1992 Nucleic Acids Research 20: 871–878.
Meyers, R.M. et al., 1986 CSHSQB 51: 275.

*Primary Examiner*—W. Gary Jones
*Assistant Examiner*—Amy Atzel
*Attorney, Agent, or Firm*—Dann, Dorfman, Herrell and Skillman

[57] ABSTRACT

An endonuclease and its method of use for the detection of mutations in targeted polynucleotide sequences are provided, which facilitate the localization and identification of mutations, mismatches and genetic polymorphisms.

17 Claims, 13 Drawing Sheets

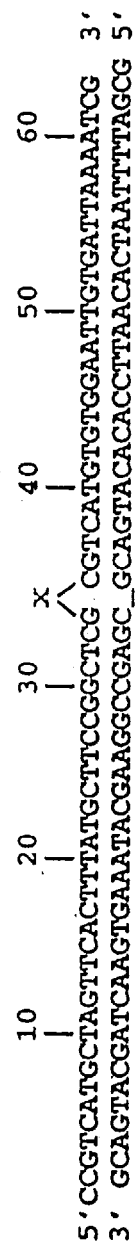
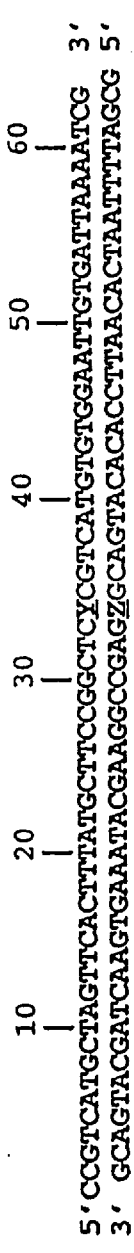

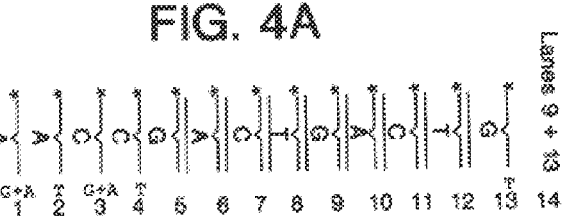
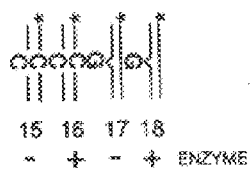
FIG. 4A
FIG. 4B
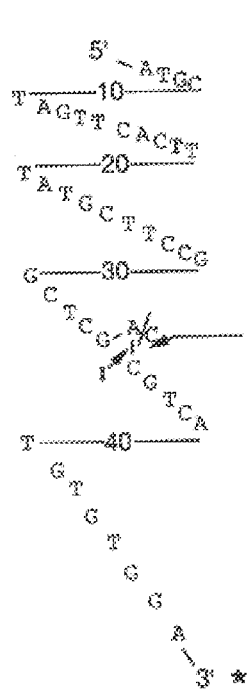
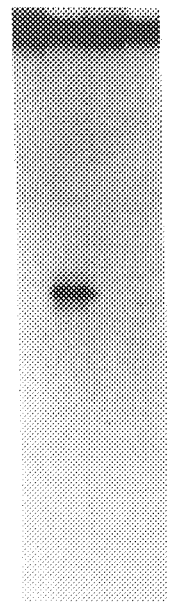

FIG. 5A
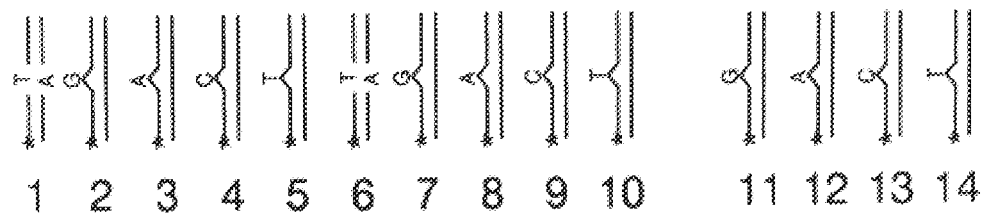
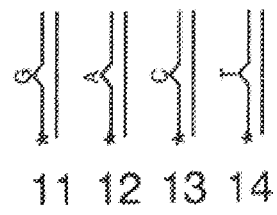
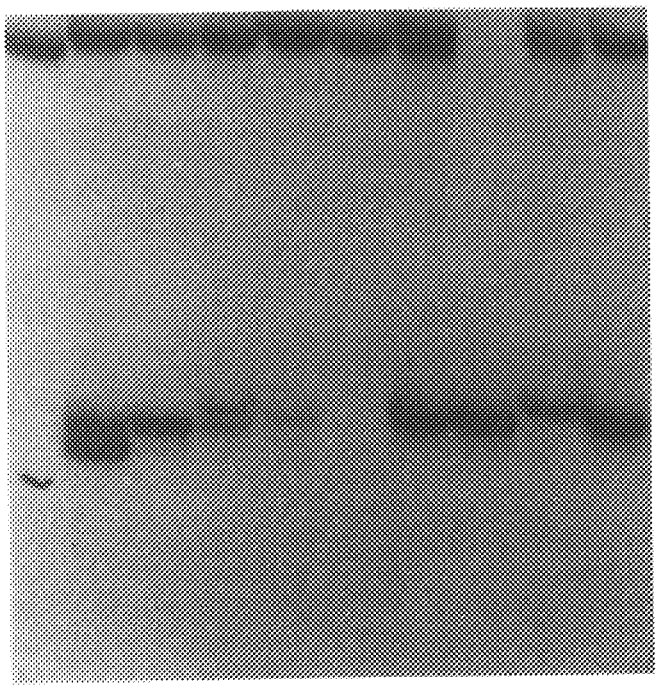
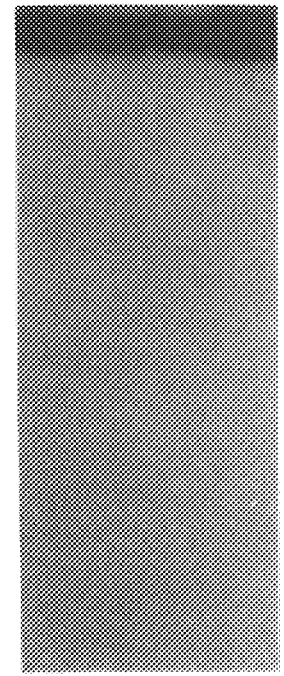
FIG. 5B          FIG. 5C
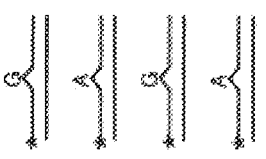
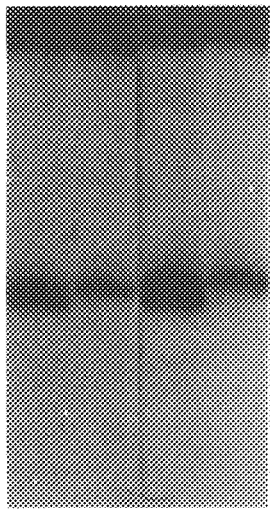

T/A A/A A/C A/G C/A C/C C/T G/A G/G G/T T/C T/G T/T

F —

I —

45°C

F —

I —

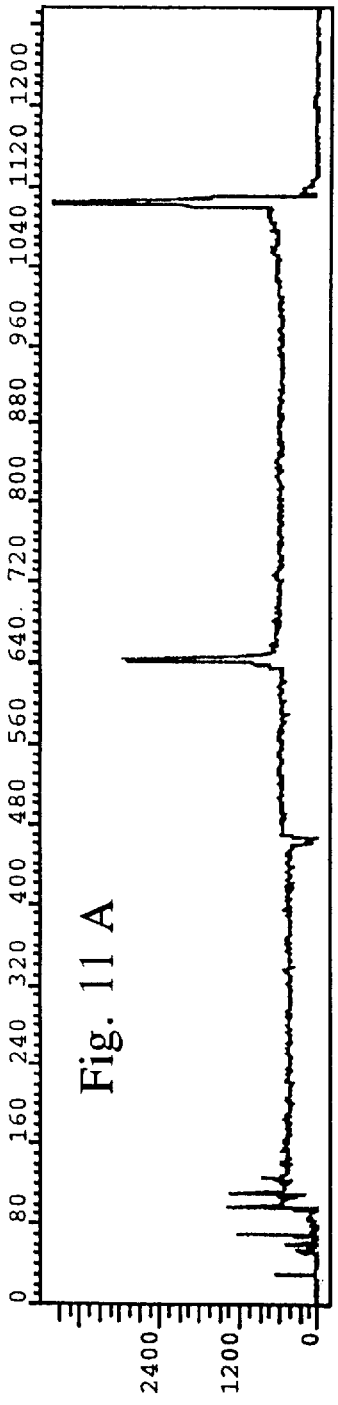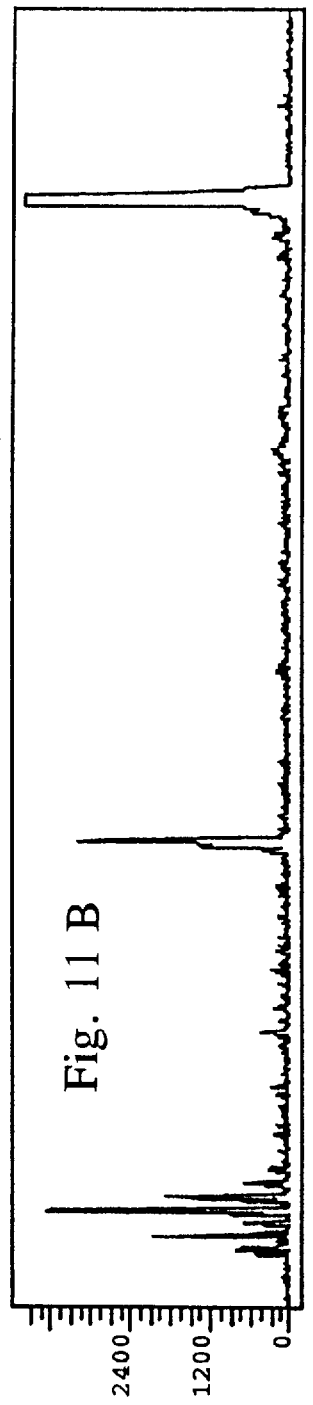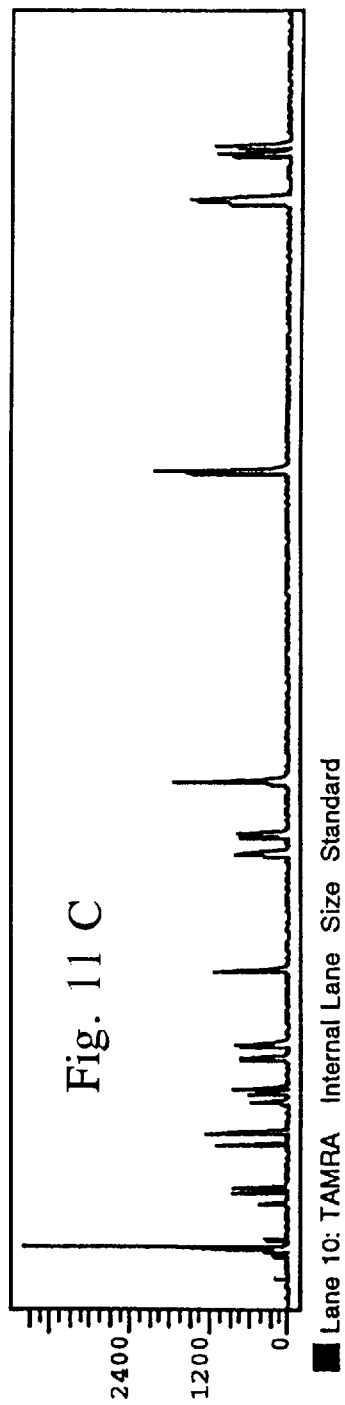

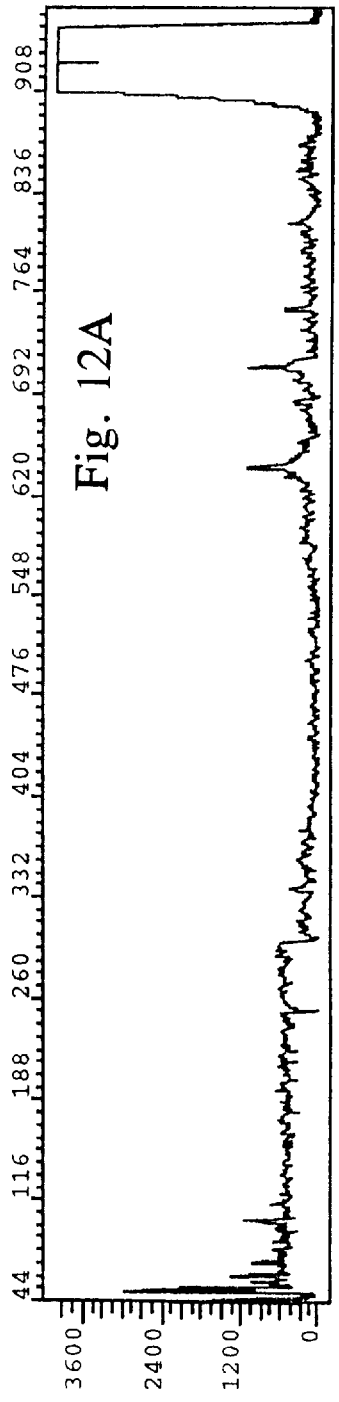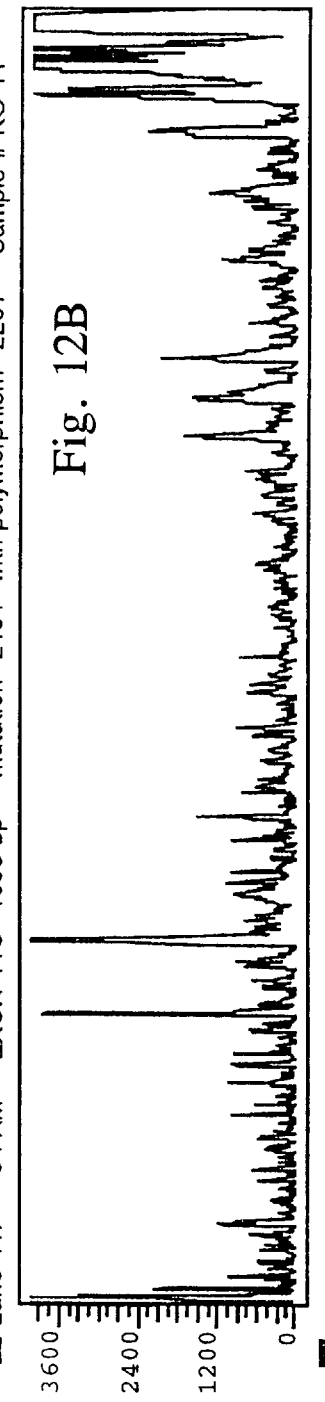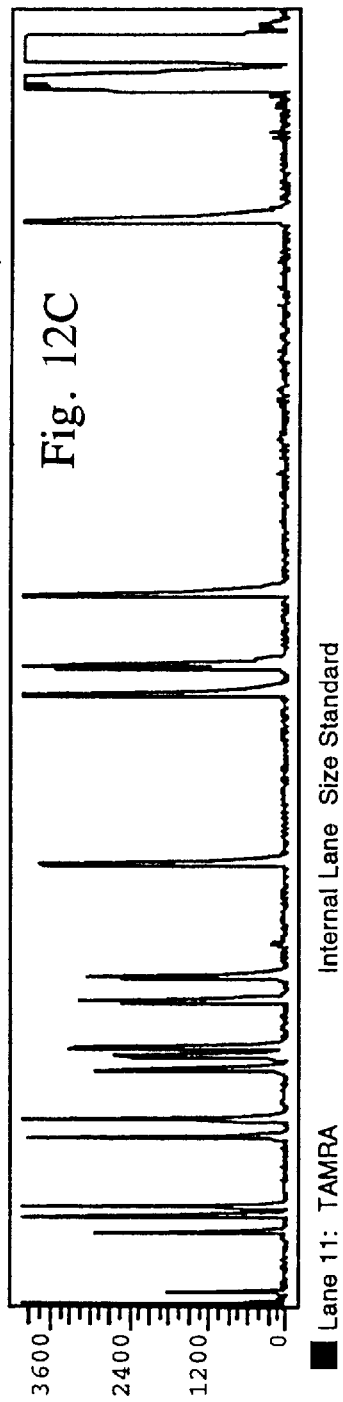

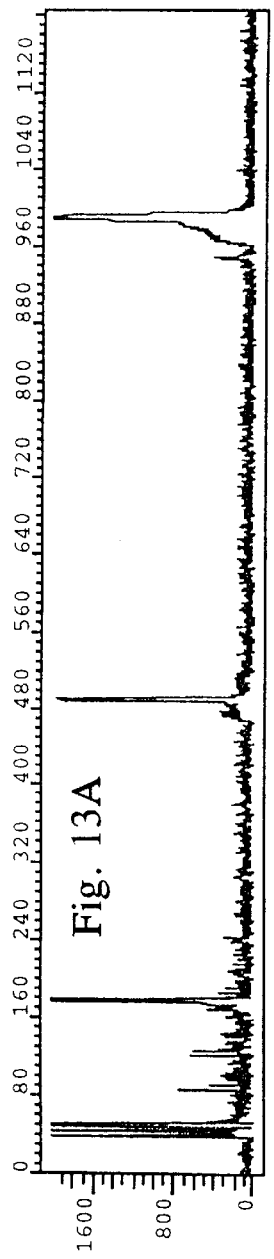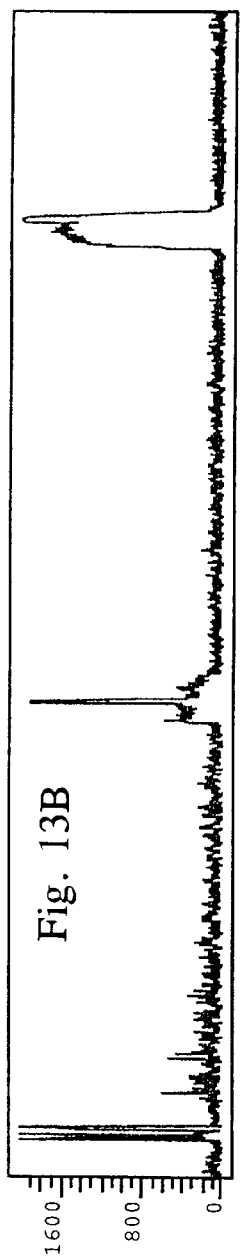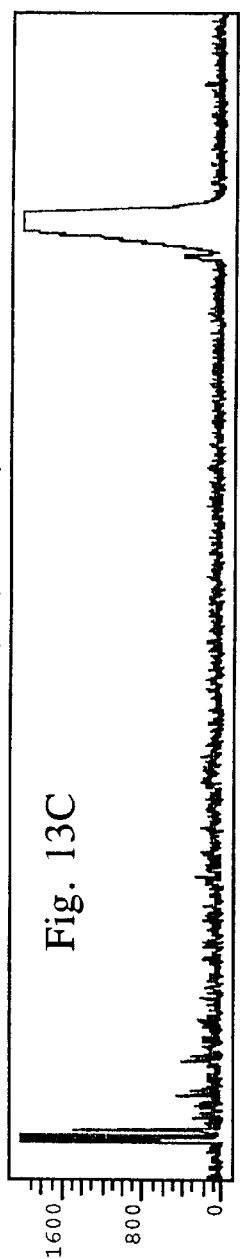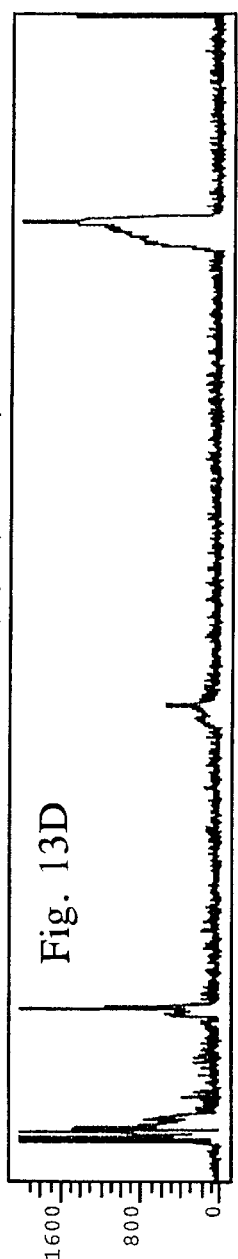

MISMATCH ENDONUCLEASE AND ITS USE IN IDENTIFYING MUTATIONS IN TARGETED POLYNUCLEOTIDE STRANDS

Pursuant to 35 U.S.C. §202(c), it is hereby acknowledged that the U.S. Government has certain rights in the invention described herein, which was made in part with funds from the National Institute of Health.

FIELD OF THE INVENTION

This invention relates to materials and methods for the detection of mutations in targeted nucleic acids. More specifically, the invention provides a novel mismatch specific nuclease and methods of use of the enzyme that facilitate the genetic screening of hereditary diseases and cancer. The method is also useful for the detection of genetic polymorphisms.

BACKGROUND OF THE INVENTION

Several publications are referenced in this application by numerals in parenthesis in order to more fully describe the state of the art to which this invention pertains. Full citations for these references are found at the end of the specification. The disclosure of each of these publications is incorporated by reference in the present specification.

The sequence of nucleotides within a gene can be mutationally altered or "mismatched" in any of several ways, the most frequent of which being base-pair substitutions, frame-shift mutations and deletions or insertions. These mutations can be induced by environmental factors, such as radiation and mutagenic chemicals; errors are also occasionally committed by DNA polymerases during replication. Many human disease states arise because fidelity of DNA replication is not maintained. Cystic fibrosis, sickle cell anemia and some cancers are caused by single base changes in the DNA resulting in the synthesis of aberrant or non-functional proteins.

The high growth rate of plants and the abundance of DNA intercalators in plants suggests an enhanced propensity for mismatch and frameshift lesions. Plants and fungi are known to possess an abundance of single-stranded specific nucleases that attack both DNA and RNA (9–14). Some of these, like the Nuclease α of *Ustilago maydis,* are suggested to take part in gene conversion during DNA recombination (15, 16). Of these nucleases, S1 nuclease from *Aspergillus oryzae* (17), and P1 nuclease from *Penicillium citrinum* (18), and Mung Bean Nuclease from the sprouts of *Vigna radiata* (19–22) are the best characterized. S1, P1 and the Mung Bean Nuclease are Zn proteins active mainly near pH 5.0 while Nuclease α is active at pH 8.0. The single strandedness property of DNA lesions appears to have been used by a plant enzyme, SP nuclease, for bulky adduct repair. The nuclease SP, purified from spinach, is a single-stranded DNase, an RNase, and able to incise DNA at $TC_{6-4}$ dimers and cisplatin lesions, all at neutral pH (23, 24). It is not yet known whether SP can incise DNA at mismatches.

In *Escherichia coli,* lesions of base-substitution and unpaired DNA loops are repaired by a methylation-directed long patch repair system. The proteins in this multienzyme system include MutH, MutL and MutS (1, 2). This system is efficient, but the C/C lesion and DNA loops larger than 4 nucleotides are not repaired. The MutS and MutL proteins are conserved from bacteria to humans, and appear to be able to perform similar repair roles in higher organisms. For some of the lesions not well repaired by the MutS/MutL system, and for gene conversion where short-patch repair systems may be more desirable, other mismatch repair systems with novel capabilities are needed.

Currently, the most direct method for mutational analysis is DNA sequencing, however it is also the most labor intensive and expensive. It is usually not practical to sequence all potentially relevant regions of every experimental sample. Instead some type of preliminary screening method is commonly used to identify and target for sequencing only those samples that contain mutations. Single stranded conformational polymorphism (SSCP) is a widely used screening method based on mobility differences between single-stranded wild type and mutant sequences on native polyacrylamide gels. Other methods are based on mobility differences in wild type/mutant heteroduplexes (compared to control homoduplexes) on native gels (heteroduplex analysis) or denaturing gels (denaturing gradient gel electrophoresis). While sample preparation is relatively easy in these assays, very exacting conditions for electrophoresis are required to generate the often subtle mobility differences that form the basis for identifying the targets that contain mutations. Another critical parameter is the size of the target region being screened. In general, SSCP is used to screen target regions no longer than about 200–300 bases. The reliability of SSCP for detecting single-base mutations is somewhat uncertain but is probably in the 70–90% range for targets less than 200 bases. As the size of the target region increases, the detection rate declines, for example in one study from 87% for 183 bp targets to 57% for targets 307 bp in length (35). The ability to screen longer regions in a single step would enhance the utility of any mutation screening method.

Another type of screening technique currently in use is based on cleavage of unpaired bases in heteroduplexes formed between wild type probes hybridized to experimental targets containing point mutations. The cleavage products are also analyzed by gel electrophoresis, as subfragments generated by cleavage of the probe at a mismatch generally differ significantly in size from full length, uncleaved probe and are easily detected with a standard gel system. Mismatch cleavage has been effected either chemically (osmium tetroxide, hydroxylamine) or with a less toxic, enzymatic alternative, using RNase A. The RNase A cleavage assay has also been used, although much less frequently, to screen for mutations in endogenous mRNA targets for detecting mutations in DNA targets amplified by PCR. A mutation detection rate of over 50% was reported for the original RNase screening method (36).

A newer method to detect mutations in DNA relies on DNA ligase which covalently joins two adjacent oligonucleotides which are hybridized on a complementary target nucleic acid. The mismatch must occur at the site of ligation. As with other methods that rely on oligonucleotides, salt concentration and temperature at hybridization are crucial. Another consideration is the amount of enzyme added relative to the DNA concentration.

The methods mentioned above cannot reliably detect a base change in a nucleic acid which is contaminated with more than 80% of a background nucleic acid, such as normal or wild type sequences. Contamination problems are significant in cancer detection wherein a malignant cell, in circulation for example, is present in extremely low amounts. The methods now in use lack adequate sensitivity to be practically applied in the clinical setting.

A method for the detection of gene mutations with mismatch repair enzymes has been described by Lu-Chang and Hsu. See WO 93/20233. The product of the MutY gene which recognizes mispaired A/G residues is employed in conjunction with another enzyme described in the reference as an "all type enzyme" which can nick at all base pair mismatches. The enzyme does not detect insertions and deletions. Also, the all type enzyme recognizes different mismatches with differing efficiencies and its activity can be adversely affected by flanking DNA sequences. This method therefore relies on a cocktail of mismatch repair enzymes and DNA glycosylases to detect the variety of mutations that can occur in a given DNA molecule.

Often, in the clinical setting, the nature of the mutation or mismatch is unknown so that the use of specific DNA glycosylases is precluded. Thus, there is a need for a single enzyme system that is capable of recognizing all mismatches with equal efficiency and also detecting insertions and deletions, regardless of the flanking DNA sequences. It would be beneficial to have a sensitive and accurate assay for detecting single base pair mismatches which does not require a large amount of sample, does not require the use of toxic chemicals, is neither labor intensive nor expensive and is capable of detecting not only mismatches but deletions and insertions of DNA as well.

Such a system, coupled with a method that would facilitate the identification of the location of the mutation in a given DNA molecule would be clearly advantageous for genetic screening applications. It is the purpose of the present invention to provide this novel mutation detection system.

SUMMARY OF THE INVENTION

The present invention provides materials and methods for the detection of mutations or mismatches in a targeted polynucleotide strand. Detection is achieved using a novel endonuclease in combination with a gel assay system that facilitates the screening and identification of altered base pairing in targeted nucleic acid strands.

According to one aspect of the invention, there is provided a novel nuclease, derived from celery and suitable for use in the detection of mutations or mismatches in target DNA or RNA. Celery (*Apium graveolens* var. dulce) contains abundant amounts of the nuclease of the invention which is highly specific for insertional/deletional DNA loop lesions and mismatches. This enzyme, designated herein as CEL I, incises at the phosphodiester bond at the 3' side of the mismatched nucleotide. CEL I has been purified about 10,000 fold, so as to be substantially homogeneous.

In a preferred embodiment of the invention, a method is provided for determining a mutation in a target sequence of single stranded mammalian polynucleotide with reference to a non-mutated sequence of a polynucleotide that is hybridizable with the polynucleotide including the target sequence. The sequences are amplified by polymerase chain reaction (PCR), labeled with a detectable marker, hybridized to one another, exposed to CEL I of the present invention, and analyzed on gels for the presence of the mutation.

The plant based endonuclease of the invention has a unique combination of properties. These include the ability to detect all possible mismatches between the hybridized sequences formed in performing the method of the invention; recognize polynucleotide loops and insertions between such hybridized sequences; detect polymorphisms between such hybridized strands; recognize sequence differences in polynucleotide strands between about 100 bp and 3 kb in length and recognize such mutations in a target polynucleotide sequence without substantial adverse effects of flanking DNA sequences.

The plant-based endonuclease, CEL I of the invention is not unique to celery. Similar enzymatic activities have been demonstrated in fourteen different plant species. Therefore, the enzyme is likely to be conserved in the plant kingdom and may be purified from plants other than celery. The procedure to purify this endonuclease activity from a plant other than celery is well known to those skilled in the art and enzymatic activity so isolated is contemplated to be within the scope of the present invention.

The plant-based endonuclease may not be limited to the plant kingdom but may be found in other life forms as well. Such enzymes may serve functions similar to that of CEL I in celery or be adapted for other special steps of DNA metabolism. Such enzymes or the genes encoding them may be used or modified to produce enzymatic activities that can function like CEL I. The isolation of such genes and their modification is also within the scope of the present invention.

In another embodiment of the invention, the above-described method is employed in conjunction with the addition of DNA ligase, DNA polymerase or a combination thereof thereby reducing non-specific DNA cleavage.

In yet another embodiment of the invention, the simultaneous analysis of multiple samples is performed using the above-described enzyme and method of the invention by a technique referred to herein as multiplex analysis.

In order to more clearly set forth the parameters of the present invention, the following definitions are used:

The term "endonuclease" refers to an enzyme that can cleave DNA internally.

The term "isolated nucleic acid" refers to a DNA or RNA molecule that is separated from sequences with which it is normally immediately contiguous (in the 5' and 3' directions) in the naturally occurring genome of the organism in which it originates.

The term "base pair mismatch" indicates a base pair combination that generally does not form in nucleic acids according to Watson and Crick base pairing rules. For example, when dealing with the bases commonly found in DNA, namely adenine, guanine, cytosine and thymidine, base pair mismatches are those base combinations other than the A-T and G-C pairs normally found in DNA. As described herein, a mismatch may be indicated, for example as C/C meaning that a cytosine residue is found opposite another cytosine, as opposed to the proper pairing partner, guanine.

The phrase "DNA insertion or deletion" refers to the presence or absence of "matched" bases between two strands of DNA such that complementarity is not maintained over the region of inserted or deleted bases.

The term "complementary" refers to two DNA strands that exhibit substantial normal base pairing characteristics. Complementary DNA may contain one or more mismatches, however.

The term "hybridization" refers to the hydrogen bonding that occurs between two complementary DNA strands.

The phrase "flanking nucleic acid sequences" refers to those contiguous nucleic acid sequences that are 5' and 3' to the endonuclease cleavage site.

The term "multiplex analysis" refers to the simultaneous assay of pooled DNA samples according to the above described methods.

The term "substantially pure" refers to a preparation comprising at least 50–60% by weight of the material of interest. More preferably, the preparation comprises at least 75% by weight, and most preferably 90–99% by weight of the material of interest. Purity is measured by methods appropriate for the material being purified, which in the case of protein includes chromatographic methods, agarose or polyacrylamide gel electrophoresis, HPLC analysis and the like.

C>T indicates the substitution of a cytosine residue for a thymidine residue giving rise to a mismatch. Inappropriate substitution of any base for another giving rise to a mismatch or a polymorphism may be indicated this way.

N,N,N',N'-tetramethyl-6-carboxyrhodamine (TAMRA) is a fluorescent dye used to label DNA molecular weight standards which are in turn utilized as an internal standard for DNA analyzed by automated DNA sequencing.

Primers may be labeled fluorescently with 6-carboxyfluorescein (6-FAM). Alternatively primers may be labeled with 4,7,2',7'-Tetrachloro-6-carboxyfluorescein (TET). Other alternative DNA labeling methods are known in the art and are contemplated to be within the scope of the invention.

CEL I has been purified so as to be substantially homogeneous, thus, peptide sequencing of the amino terminus is envisioned to provide the corresponding specific oligonucleotide probes to facilitate cloning of the enzyme from celery. Following cloning and sequencing of the gene, it may be expressed in any number of recombinant DNA systems. This procedure is well known to those skilled in the art and is contemplated to be within the scope of the present invention.

BRIEF DESCRIPTION OF THE DRAWINGS

FIG. 2 depicts certain heteroduplex DNA substrates used in performing nucleic acid analyses in accordance with the present invention. FIG. 2A depicts a 64-mer which can be terminally labeled at either the 5'-P or the 3'-OH. The nucleotide positions used as a reference in this analysis are indicated irrespective of the number of nucleotide insertions at X in the top strand. The inserted sequences and substrate numbers are indicated in the table. FIG. 2B illustrates mismatched basepair substrates used in this analysis, with the identities of nucleotides Y and Z varied as in the accompanying table to produce various mispaired substrates.

FIG. 4 is an autoradiogram illustrating the relative incision preferences of CEL I at DNA loops of one nucleotide. FIG. 4A shows that in addition to the X=G, the X=C also allows two alternate basepairing conformations. FIG. 4B demonstrates that the bottom strand of the substrate is competent for CEL I incision as in the C/C mismatch, #10, in lane 16.

FIG. 5 is an autoradiogram of denaturing 15% polyacrylamide gels showing the AmpliTaq DNA polymerase mediated stimulation of purified CEL I incision at DNA mismatches of a single extrahelical nucleotide. F indicates the full length substrate, 64 nucleotide long, labeled at the 5' terminus (*) of the top strand. In panels 5A, 5B and 5C, substrates were treated with varying quantities of CEL I in the presence or absence of DNA polymerase.

FIG. 11 is a histogram of a sample showing the localization of a 5 base deletion in the 11D exon of BRCA1 following PCR amplification and treatment with CEL I. A spike indicates a DNA fragment of a specific size generated by cleavage by CEL I at the site of a mismatch. Panel A shows the results obtained with a 6-FAM labeled primer annealed at nucleotide 3177 of BRCA1. Panel B shows the results obtained with a TET labeled primer annealed 73 bases into the intron between exon 11 and exon 12. Panel C represents the TAMRA internal lane size standard. Note that the position of the mutation can be assessed on both strands of DNA.

FIG. 12 is a histogram of a sample showing the localization of nonsense mutation, A>T, at position 2154 and a polymorphism C>T at nucleotide 2201 in the 11C exon of BRCA1 following PCR amplification and treatment with CEL I. Panel A shows a spike at base #700 and Panel B shows a spike at #305 corresponding to the site of the nonsense mutation. Panel C is the TAMRA internal lane standard.

FIG. 13 shows the results obtained from four different samples analyzed for the presence of mutations in exon 11A using the methods of the instant invention. Results from the 6-FAM samples are shown. Panel A shows a polymorphism T>C at nucleotide 2430 and a second spike at position #483 corresponding to the site of another polymorphism C>T at nucleotide 2731. Panel B shows only the second polymorphism described in panel A. Panel C shows no polymorphism or mutation. Panel D shows the two polymorphisms seen in panel A.

DETAILED DESCRIPTION OF THE INVENTION

Figure 1:
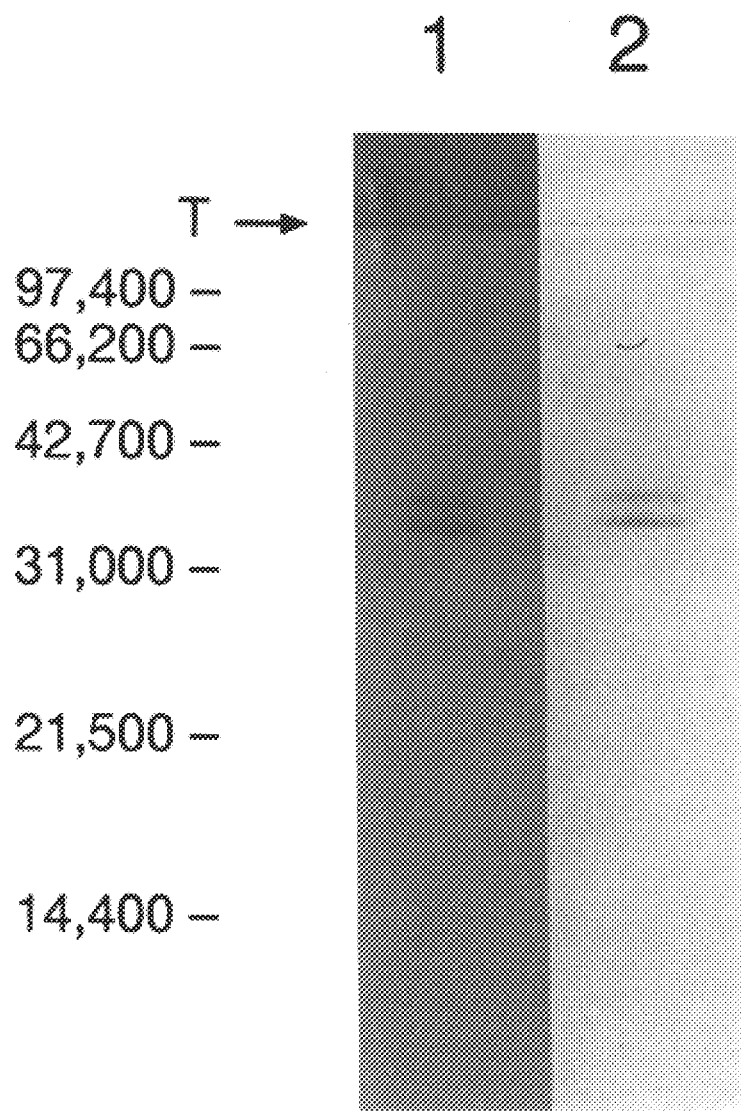
FIG. 1 shows the results of sodium dodecyl sulfate (SDS) polyacrylamide gel analysis of the purified enzyme, CEL I. The positions of molecular weight markers are shown on the side. T indicates the top of the resolving gel.

The enzymatic basis for the maintenance of correct base sequences during DNA replication has been extensively studied in *E. coli*. This organism has evolved a mismatch repair pathway that corrects a variety of DNA basepair mismatches in hemimethylated DNA as well as insertions/deletions up to four nucleotides long. Cells deficient in this pathway mutate more frequently, hence the genes are called MutS, MutL and MutH etc. MutS protein binds to the mismatch and MutH is the endonuclease that incises the DNA at a GATC site on the strand in which the A residue is not methylated. MutL forms a complex with MutH and MutS during repair. Homologs of MutS and MutL, but not MutH exist in many systems. In yeast MSH2 (MutS homolog) can bind to a mismatch by itself, but a complex of two MutL homologs (MLH and PMS1) plus a MSH2 has been observed. The human homolog hMSH2 has evolved to bind to larger DNA insertions up to 14 nucleotides in length, which frequently arise by mechanisms such as misalignment at the microsatelite repeats in humans. A role for hMLH1 in loop repair is unclear. Mutations in any one of these human homologs were shown to be responsible for the hereditary form of non-polyposis colon cancer (27, 28).

Celery contains over 40 μg of psoralen, a photoreactive intercalator, per gram of tissue (3). As a necessity, celery may possess a high capability for the repair of lesions of insertion, deletion, and other psoralen photoadducts. Single-strandedness at the site of the lesion is common to base substitution and DNA loop lesions. The data in the following examples demonstrate that celery possesses ample mismatch-specific endonuclease to deal with these potentially mutagenic events.

It has been found that the incision at a mismatch site by CEL I is greatly stimulated by the presence of a DNA polymerase. For a DNA loop containing a single nucleotide insertion, CEL I substrate preference is A≧G>T>C. For base-substitution mismatched basepairs, CEL I preference is C/C≧C/A~C/T≧G/G>A/C~A/A~T/C>T/G~G/T~G/A~A/G>T/T. CEL I shows a broad pH optimum from pH 6 to pH 9. To a lesser extent compared with loop incisions, CEL I is also a single-stranded DNase, and a weak exonuclease. CEL I possesses novel biochemical activities when compared to other nucleases. Mung Bean Nuclease is a 39 kd nuclease that is a single-stranded DNase and RNase, and has the ability to nick DNA at destabilized regions and DNA loops (19–22). However, it has a pH optimum at 5.0. It is not known whether Mung Bean Nuclease activity can be stimulated by a DNA polymerase as in the case of CEL I. Thus CEL I and Mung Bean Nuclease appear to be different enzymes; however this has not yet been conclusively confirmed.

The mechanism responsible for the AmpliTaq DNA polymerase stimulation of the CEL I activity is presently unknown. One possibility is that the DNA polymerase has a high affinity for the 3'—OH group produced by the CEL I incision at the mismatch and displaces CEL I simply by competition for the site. CEL I may have different affinities for the 3'—OH termini generated by incisions at different mismatches, thereby attenuating the extent that AmpliTaq DNA polymerase can stimulate its activity. The use of a DNA polymerase to displace a repair endonuclease in DNA repair was also observed for the UvrABC endonuclease mechanism (25). It was shown that the UvrABC endonuclease does not turnover unless it is in the presence of DNA polymerase I. The protein factors in vivo that can stimulate the CEL I activity may not be limited to DNA polymerases. It is possible that DNA helicases, DNA ligases, 3'-5' exonucleases or proteins that bind to DNA termini may perform that function.

It is important to note that a 5'-labeled substrate can be used to show a CEL I incision band in a denaturing polyacrylamide gel. Recently, a putative human all-type mismatch incision activity (24) was shown to be related to the human topoisomerase I. This enzyme is unable to release itself from a 5'-labeled substrate after mismatch nicking due to the formation of a covalent enzyme-DNA intermediate with the 3' terminus of the DNA nick (26). This covalent protein-DNA complex cannot migrate into the denaturing polyacrylamide gel to form a band. CEL I mismatch nicking has been demonstrated with 5' labeled substrates. Therefore, CEL I is not a plant equivalent of the topoisomerase I-like human all-type mismatch repair activity.

CEL I appears to be a mannopyranosyl glycoprotein as judged by its tight binding to Concanavalin A-Sepharose resin and by the staining of CEL I with the Periodic acid-Schiff glycoprotein stain. Insofar as it is known, no repair enzyme has been demonstrated to be a glycoprotein. Glycoproteins are often found to be excreted from the cell, on cellular membranes or secreted into organelles. However, glycoproteins have also been shown to exist in the nucleus for important functions. The level of a 100 kDa stress glycoprotein was found to increase in the nucleus when Gerbil fibroma cells are subjected to heat shock treatment (27). Transcription factors for RNA polymerase II in human cells are known to be modified with N-acetylglucosamine residues (28, 29). Recently, lactoferrin, an iron-binding glycoprotein, was found to bind to DNA in the nucleus of human cells and it activated transcription in a sequence-specific manner (30). The nuclei of cells infected with some viruses are known to contain viral glycoproteins (31–33). These examples where glycoproteins are known to exist inside the nucleus, not merely on the nuclear membrane or at the nuclear pores, tend to show that glycosylated proteins may be important in the nucleus. CEL I appears to be an example of a glycoprotein that can participate in DNA repair.

The properties of the celery mismatch endonuclease CEL I resemble those of single-stranded nucleases. The best-suited substrates for CEL I are DNA loops and base-substitution mismatches such as the C/C mismatch. In contrast, loops greater than 4 nucleotides and the C/C mismatch are the substrates worst-suited for the *E. coli* mutHLS mismatch repair system (1, 2). Thus CEL I is an enzyme that possesses novel mismatch endonuclease activity.

The following examples are provided to describe the invention in further detail. These examples, which set forth the best mode presently contemplated for carrying out the invention, are intended to illustrate and not to limit the invention.

EXAMPLE I

Purification of CEL I

Two different CEL I preparations were made up as described below. Their properties are similar except that the less pure preparation (Mono Q fraction) may contain protein factors that can stimulate the CEL I activity.

(i) Preparation of CEL I Mono Q fraction 100 gm of celery stalk was homogenized in a Waring blender with 100 ml of a buffer of 0.1M Tris-HCl pH 7.0 with 10 μM phenylmethanesulfonyl fluoride (PMSF) (Buffer A) at 4° C. for 2 minutes. The mixture was cleared by centrifugation, and the supernatant was stored at −70° C. The extract was fractionated by anion exchange chromatography on a FPLC Mono Q HR5/10 column. The bound CEL I nuclease activity was eluted with a linear gradient of salt at about 0.15M KCl.

(ii) Preparation of highly purified CEL I

7 Kg of celery at 4° C. was extracted with a juicer and adjusted with 10X Buffer A to give a final concentration of 1X Buffer A. The extract was concentrated with a 25% to 85% saturation ammonium sulfate precipitation step. The final pellet was dissolved in 250 ml of Buffer A and dialyzed against 0.5M KCl in Buffer A. The solution was incubated with 10 ml of Concanavalin A-Sepharose resin (Sigma) overnight at 4° C. The slurry was packed into a 2.5 cm diameter column and washed with 0.5M KCl in Buffer A. The bound CEL I was eluted with 60 ml of 0.3M α-D mannose, 0.5M KCl in Buffer A at 65° C. The CEL I was dialyzed against a solution of 25 mM $KPO_4$, 10 μM PMSF, pH 7.4 (Buffer B), and applied to a phosphocellulose column that had been equilibrated in the Buffer B. The bound enzyme was eluted with a linear gradient of KCl in Buffer B. The peak of CEL I activity from this column was further fractionated by size on a Superose 12 FPLC column in 0.2M KCl, 1 mM $ZnCl_2$, 10 μM PMSF, 50 mM Tris-HCl pH 7.8. The center of the CEL I peak from this gel filtration step was used as the purified CEL I in this study. A protein band of about 34,000 daltons is visible when 5 micrograms of CEL I of the Superose 12 fraction was visualized with Coomassie Blue staining or carbohydrate staining (Periodic acid-Schiff base mediated staining kit, SIGMA Chemicals (5)) on a 15% polyacrylamide SDS PAGE gel as shown in FIG. 1. A second band of approximately 36,000 daltons was also visible in the gel. Both bands were stained with the glycoprotein specific stain. The subtle mobility differences observed in the two bands may be due to differential glycosylation. Alternatively, there may be a contaminant in the preparation which co-purifies with CEL I.

Protein determination

Protein concentrations of the samples were determined by the Bicinchoninic acid protein assay (4, Pierce).

Following purification of CEL I enzyme, mutational analysis on experimental and clinical DNA substrates were performed in a suitable gel system. CEL I recognized and cleaved DNA at a variety of mismatches, deletions and insertions. The following examples describe in greater detail the manner in which mutational analysis is practiced according to this invention.

EXAMPLE II

Preparation of heteroduplexes containing various mismatches

DNA heteroduplex substrates of 64 basepairs long were constructed containing mismatched basepairs or DNA loops which were prepared using similar methods reported in Jones and Yeung (34). The DNA loops are composed of different nucleotides and various loop sizes as illustrated in FIG. 2. The DNA duplexes were labeled at one of the four termini so that DNA endonuclease incisions at the mispaired nucleotides could be identified as a truncated DNA band on a denaturing DNA sequencing gel. The oligonucleotides were synthesized on an Applied Biosystems DNA synthesizer and purified by using a denaturing PAGE gel in the presence of 7M urea at 50° C. The purified single-stranded oligonucleotides were hybridized with appropriate opposite strands. The DNA duplex, containing mismatches or not, was purified by using a nondenaturing PAGE gel. DNA was eluted from the gel slice by using electro-elution in a Centricon unit in an AMICON model 57005 electroeluter. The upper reservoir of this unit has been redesigned to include water-tight partitions that prevent cross-contamination. The sequences of the substrates used are set forth below:

SEQ. I.D. No. 2 is the top strand of Substrate Nos. 1, 12, 13, and 14: 5'-CCGTCATGCT AGTTCACTTT ATGCTTC-CGG CTCGCGTCAT GTGTGGAATT GTGATTAAAA TCG-3';

SEQ. I.D. No. 3 is the bottom strand of Substrate Nos. 1, 2, 3, 4, 5, 7, 10, 15:
5'-GCGATTTTAA TCACAATTCC ACACATGACG CGAGCCGGAA GCATAAAGTG, AACTAGCATG ACG-3';

SEQ. I.D. No. 4 is the top strand of Substrate No. 2: 5'-CCGTCATGCT AGTTCACTTT ATGCTTCCGG CTCGGCGTCA TGTGTGGAAT TGTGATTAAA ATCG-3';

SEQ. I.D. No. 5 is the top strand of Substrate No. 3: 5'-CCGTCATGCT AGTTCACTTT ATGCTTCCGG CTCGTCGTCA TGTGTGGAAT TGTGATTAAA ATCG-3';

SEQ. I.D. No. 6 is the top strand of Substrate No. 4: 5'-CCGTCATGCT AGTTCACTTT ATGCTTCCGG CTCGACGTCA TGTGTGGAAT TGTGATTAAA ATCG-3';

SEQ. I.D. No. 7 is the top strand of Substrate No. 5: 5'-CCGTCATGCT AGTTCACTTT ATGCTTCCGG CTCGCCGTCA TGTGTGGAAT TGTGATTAAA ATCG-3';

SEQ. I.D. No. 8 is the top strand of Substrate Nos. 6, 7, 8, 18: 5'-CCGTCATGCT AGTTCACTTT ATGCTTCCGG CTCACGTCAT GTGTGGAATT GTGATTAAAA TCG-3';

SEQ. I.D. No. 9 is the top strand of Substrate Nos. 9, 10, 11, 19: 5'-CCGTCATGCT AGTTCACTTT ATGCTTCCGG CTCCCGTCAT GTGTGGAATT GTGATTAAAA TCG-3';

SEQ. I.D. No. 10 is the top strand of Substrate Nos. 15, 16, 17, 20: 5'-CCGTCATGCT AGTTCACTTT ATGCTTC-CGG CTCTCGTCAT GTGTGGAATT GTGATTAAAA TCG-3';

SEQ. I.D. No. 11 is the bottom strand of Substrate Nos. 6, 9, 12, 20: 5'-GCGATTTTAA TCACAATTCC ACACAT-CACG AGAGCCGGAA GCATAAAGTG AACTAG-CATG ACG-3';

SEQ. I.D. No. 12 is the bottom strand of Substrate Nos. 8, 13, 16, 19: 5'-GCGATTTTAA TCACAATTCC ACACAT-CACG GGAGCCGGAA GCATAAAGTG AACTAG-CATG ACG-3';

SEQ. I.D. No. 13 is the bottom strand of Substrate Nos. 11, 14, 17, 18: 5'-GCGATTTTAA TCACAATTCC ACACAT-CACG TGAGCCGGAA GCATAAAGTG AACTAG-CATG ACG-3'.

EXAMPLE III

Mismatch endonuclease assay

Fifty to 100 fmol of 5' [$^{32}$P]-labeled substrate described in Example II were incubated with the Mono Q CEL I preparation in 20 mM Tris-HCl pH 7.4, 25 mM KCl, 10 mM $MgCl_2$ for 30 minutes at temperatures of 0° C. to 80° C. From one half to 2.5 units of AmpliTaq DNA polymerase was added to the nuclease assay reaction. Ten μM dNTP was included in the reaction mixture where indicated (FIGS. 2 & 5). The 20 μL reaction was terminated by adding 10 μL of 1.5% SDS, 47 mM EDTA, and 75% formamide plus tracking dyes and analyzed on a denaturing 15% PAGE gel in 7M urea at 50° C. An autoradiogram was used to visualize the radioactive bands. Chemical DNA sequencing ladders were included as size markers. Incision sites were accurately determined by co-electrophoresis of the incision band and the DNA sequencing ladder in the same lane.

EXAMPLE IV

Figure 3:
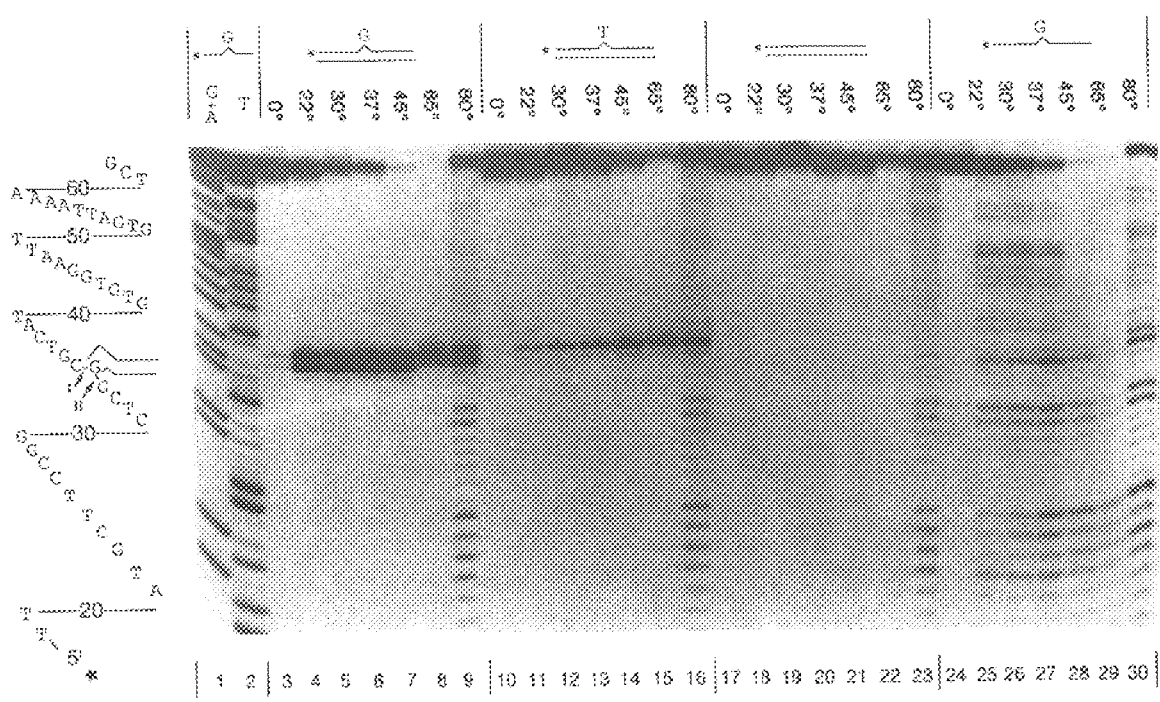
FIG. 3 is an autoradiogram demonstrating the effect of temperature on CEL I incisions in different substrates.

The Effect of Temperature on CEL I Incision Activity at single-nucleotide DNA loop and nucleotide substitutions The CEL I fraction eluted from the Mono Q chromatography of the celery extract was found to specifically nick DNA heteroduplexes containing DNA loops with a single extrahelical guanine (substrate #2) or thymine residue (#3), but not the perfectly basepaired DNA duplex #1 as shown in FIG. 3. In these experiments fifty fmol of heteroduplex #2 (lanes 3–9), #3 (lanes 10–16), perfectly basepaired duplex #1 (lanes 17–23) and single-stranded DNA substrate (lanes 24–30), each labeled at the 5'-terminus with γ-[$^{32}$p] ATP and T4 polynucleotide kinase at about 6000 Ci/mmol, were incubated with 0.5 μL (10 μg) of the Mono Q fraction of the CEL I preparation in 20 mM Tris-HCl pH 7.4, 25 mM KCl, 10 mM MgCl$_2$ for 30 minutes at various temperatures. Each 20 μL reaction was terminated by adding 10 μL of 1.5% SDS, 47 mM EDTA, and 75% formamide containing xylene cyanol and bromophenol blue. Ten μL of the sample was loaded onto a 15% polyacrylamide, 7M urea denaturing DNA sequencing gel at about 50° C., and subjected to electrophoretic separation and autoradiography as previously reported (7). The G+A and the T chemical sequencing reactions were performed as described (7) and used as size markers. CEL I incision produced bands at about 35 nucleotides long. Lines are drawn from the positions of the incision bands to the phosphodiester bonds (I and II) nicked by the endonuclease in the reference sequencing ladder. For a 5'-labeled substrate, when a nuclease nicks 5' of a nucleotide and produces a 3'-OH terminus, the truncated band runs half a nucleotide spacing slower than the band for that nucleotide in the chemical DNA sequencing reaction product lane (34).

Substrate #2 can basepair in two conformations because the inserted G is within a CGCG sequence. Therefore either the G residue in the second or the third nucleotide position can become unpaired, possibly extrahelical in conformation, when this duplex is hybridized:

5'-CGGCG-3' or 5'-CGGCG-3'
3'-G-CGC-5' 5'-GC-GC-5'

Accordingly, two mismatch incision bands were observed, each correlating to the phosphodiester bond immediately 3' of the unpaired nucleotide. See FIG. 3, lanes 3–9. This slippage can occur in the target sequence only when G or C is in the mismatched top strand. Therefore, the non-paired T residue in substrate #3 gave one incision band at the same relative position as the upper band derived from the substrate #2. See FIG. 3, lanes 10–16. These gel mobilities are consistent with the production of a 3'-OH group on the deoxyribose moiety (6). CEL I increases in activity with temperature up to 45° C. as illustrated by the increase in band intensity, see FIG. 3. However, from 65° C. to 80° C., specificity is diminished due to DNA duplex denaturation.

EXAMPLE V

Relative Incision Preferences of CEL I

To ascertain whether there is a single endonuclease incision at each DNA duplex, the experiment described in FIG. 3 was repeated with DNA labeled on the 3' terminus of the top strand. If there were only one incision site, initial incision positions revealed by substrates labeled at the 5' or the 3' termini should be at the same phosphodiester bond. In these experiments, substrates were labeled at the 3' termini with [$^{32}$P] α-dCTP, cold dGTP and the Klenow fragment of DNA polymerase I to about 6000 Ci/mmol. The sample preparation, denaturing gel resolution and autoradiogram analysis are the same as described in FIG. 3 except incubation of 50 fmole of substrate with 10 μg of the CEL I Mono Q fraction was for 30 minutes at a single temperature, 37° C. The DNA sequencing ladders for substrates #4 and #5 are shown in lanes 1–4 to illustrate the DNA sequences used. Lanes 5–8 had no enzyme during the incubation. Lanes 9–12 are mismatch endonuclease incisions of the substrates #2, #4, #5, #3, respectively. A line is drawn from the position of the incision band to the phosphodiester bond (I) nicked by the endonuclease in the reference sequencing ladder. Lanes 13 and 14 demonstrate the coelectrophoresis of the CEL I incision band with a chemical DNA sequencing ladder to accurately determine the incision position. Relative incision preferences for substrates #2, #3, #4, and #5 are shown in FIG. 4 for the 3' labeled substrates. The mobilities of the incision bands in lanes 9–12 of FIG. 4 indicate that the incision reactions had occurred at the phosphodiester bond immediately 3' of the unpaired nucleotide. Therefore, the incision site is the same for substrates labeled either at the 5' or the 3' terminus. The fact that the DNA incision was found to occur at the same bond position, whether the substrate DNA was labeled at the 5' termini or the 3' termini shows that CEL I is not a DNA glycosylase. A DNA glycosylase mechanism would cause the DNA incision position in the two DNA substrates to be one base apart because a base is excised by the DNA glycosylase.

Precise determination of the incision site was performed as in the example in lane 14 in which the T residue chemical sequencing reaction of the labeled top strand of substrate #2 (lane 13) was mixed with the CEL I incision product of lane 9 and analyzed in the same lane. For a 3'-labeled substrate, when a nuclease nicks 3' of a nucleotide and produces a 5' PO$_4$ terminus, the truncated band runs with the band for that nucleotide in the chemical DNA sequencing reaction product lane (7). Moreover, the gel mobility, relative to the size standards of chemical DNA sequencing, illustrated that the DNA nick produced a 5'-phosphorylated terminus (6). For a DNA loop with a single nucleotide insertion, the nuclease specificity is A≧G>T>C. It can be seen in FIG. 4A that a small amount of 5' to 3' exonuclease activity is present in this CEL I preparation.

To test whether CEL I can cut in the bottom strand across from a DNA loop of one nucleotide in the top strand, or whether nicking of the loop-containing strand may lead to secondary CEL I incision across from the nick, the bottom strand that contains no unpaired nucleotides in substrate #2 was labeled at the 3' end and incubated in the presence of CEL I. The extrahelical nucleotide in the top strand, or the DNA nick made by CEL I in the top strand of substrate #2, seen in lane 9 of FIG. 4, did not lead to significant nicking of the bottom strand (lane 18). As a control against the possibility that DNA sequence effect may favor CEL I incision in the top strand and not the bottom strand, CEL I was tested for incision of the bottom strand in the C/C mismatch substrate in lanes 15 and 16. Mismatch incision was made when CEL I was present in lane 16.

In the characterization of the incision site of a repair endonuclease, it is important to determine whether one or two incisions have been made for each lesion. This is normally accomplished by using lesion-containing substrates that have been labeled, in turn, at the four termini of a DNA duplex. This test has been satisfied in the analysis of substrate #2 by using three labeled substrates because of the near absence of incision in the bottom strand. In FIG. 3, lane 4–7 and FIG. 4, lane 9, respectively, the incision of this substrate in both the 5' labeled and the 3' labeled substrates have been compared. The incision site was found to be at the 3' side of the mismatched nucleotide in both cases. The lack of incision on the bottom strand for substrate #2 was demonstrated in lane 18 of FIG. 4. Only the 5' labeled substrate was needed in this case since no significant bottom strand incision had occurred.

EXAMPLE VI

Effect of AmpliTaq DNA polymerase on the incisions at DNA loop mismatches

CEL I activity is stimulated by the presence of a DNA polymerase. In FIG. 5, the CEL I incisions at single-nucleotide loop substrates were stimulated by AmpliTaq DNA polymerase to different extents depending on which nucleotides are present in the loop. It was necessary to use different amounts of CEL I to illustrate the AmpliTaq DNA polymerase stimulation. The stimulation of the incision at extrahelical C and extrahelical T substrates are best illustrated in FIGS. 5 A & B (compare lanes 4 with lanes 9, and lanes 5 with lanes 10, in the respective panels) where higher CEL I levels are required to show good incision at these mismatches. For extrahelical G and extrahelical A substrates that are among the best substrates for CEL I, AmpliTaq DNA polymerase stimulation can best be illustrated by using a much lower level of CEL I as in FIG. 5. The amounts of AmpliTaq stimulation of CEL I in FIG. 5 were quantified and presented in Table I.

TABLE I

Quantification of the CEL I incision bands shown in the autoradiogram in FIG. 5.

| AmpliTaq Substrate | – Panel lane# | Counts | + Panel lane# | Counts | +/– |
| --- | --- | --- | --- | --- | --- |
| Extrahelical G, band I | A,2 | 20894 | A,7 | 22101 | 1.1 |
| Extrahelical A, band I | A,3 | 19451 | A,8 | 26357 | 1.4 |
| Extrahelical C, band I | A,4 | 4867 | A,9 | 12009 | 2.5 |
| Extrahelical T, band I | A,5 | 2297 | A,10 | 25230 | 11.0 |
| Extrahelical G, band I | B,2 | 12270 | B,7 | 19510 | 1.6 |
| Extrahelical A, band I | B,3 | 10936 | B,8 | 24960 | 2.3 |
| Extrahelical C, band I | B,4 | 1180 | B,9 | 2597 | 2.2 |
| Extrahelical T, band I | B,5 | 700 | B,10 | 21086 | 30.1 |
| Extrahelical G, band I | C,11 | 10409 | C,13 | 18649 | 1.8 |
| Extrahelical G, band II | C,11 | 9020 | C,13 | 19912 | 2.2 |
| Extrahelical A, band I | C,12 | 7165 | C,14 | 14983 | 2.1 |

The Autoradiograms were quantified in two dimensions with an AMBIS densitometer and the amount of signal in each band is given as counts.

EXAMPLE VII

Optimum pH of CEL I Activity

Figure 6A:
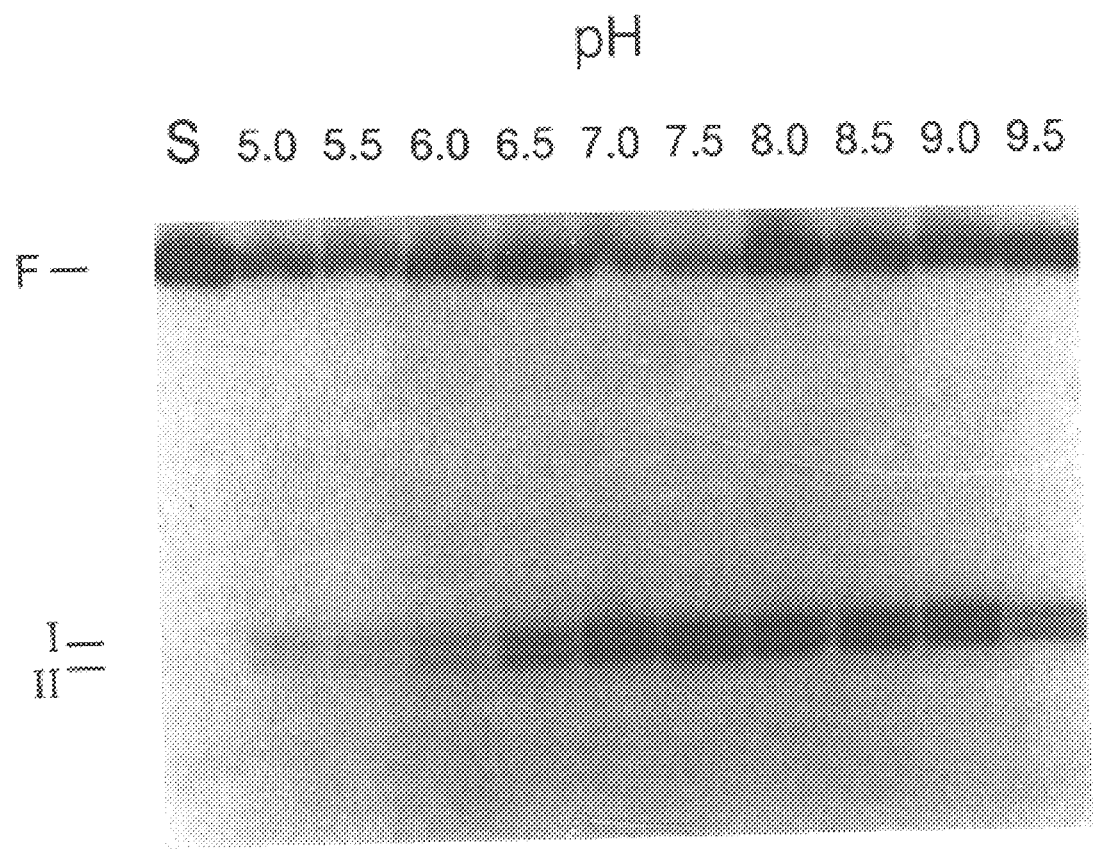
FIG. 6 is an autoradiogram showing the pH optimum of CEL I incision at the extrahelical G residue in the presence or absence of AmpliTaq DNA polymerase. The top panel shows the CEL I activity in the absence of AmpliTaq DNA polymerase. The bottom panel shows CEL I activity in the presence of polymerase.
Figure 6B:
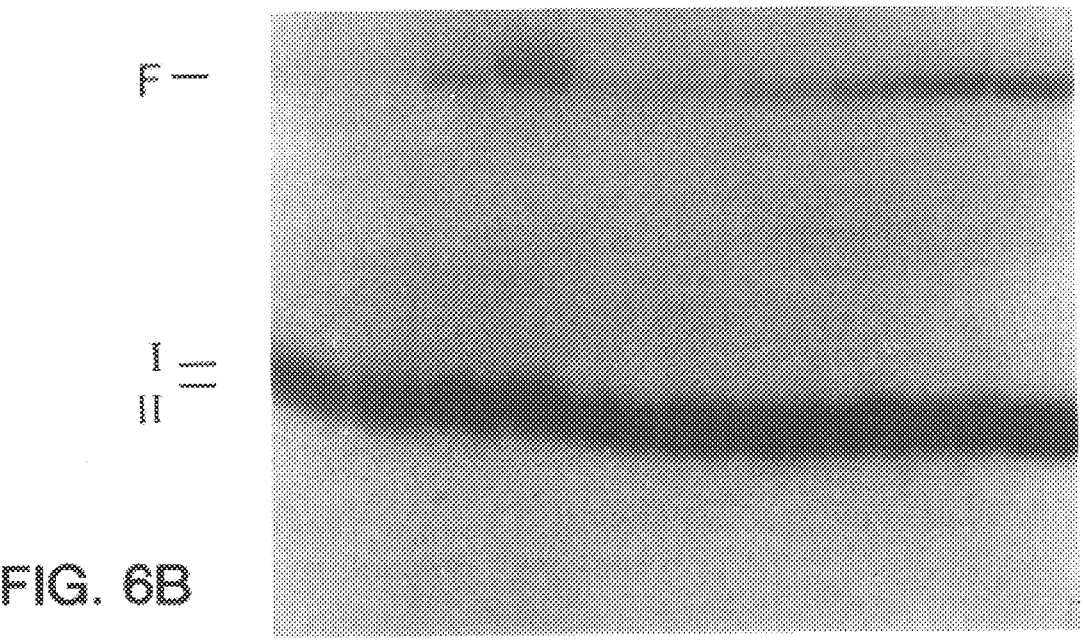

The pH optimum of CEL I for the extrahelical G substrate was investigated in the absence or presence of the AmpliTaq DNA polymerase. CEL I (9.5 ng) was incubated with 100 fmol of the substrate in a 20 µL reaction in buffers of pH 5–6.5 (imidazole) and pH 7–9.5 (Tris-HCl) for 30 minutes at 37° C. When used, one half unit of AmpliTaq DNA polymerase was present in the incubation in the top (–polymerase) or bottom panels (+polymerase), respectively. As shown in FIG. 6, CEL I was found to be active from pH 5.0 to pH 9.5, and showed a broad pH optimum centered about pH 7.5 (top panel). When AmpliTaq DNA polymerase was present, the incision was stimulated across the whole pH range (bottom panel). The assay method did not use initial kinetics and thus precluded quantitative conclusions on this pH profile of CEL I. However, it is clear that the enzyme works very well in the neutral pH ranges.

EXAMPLE VIII

Incisions by CEL I at basepair substitutions

Figure 7A:
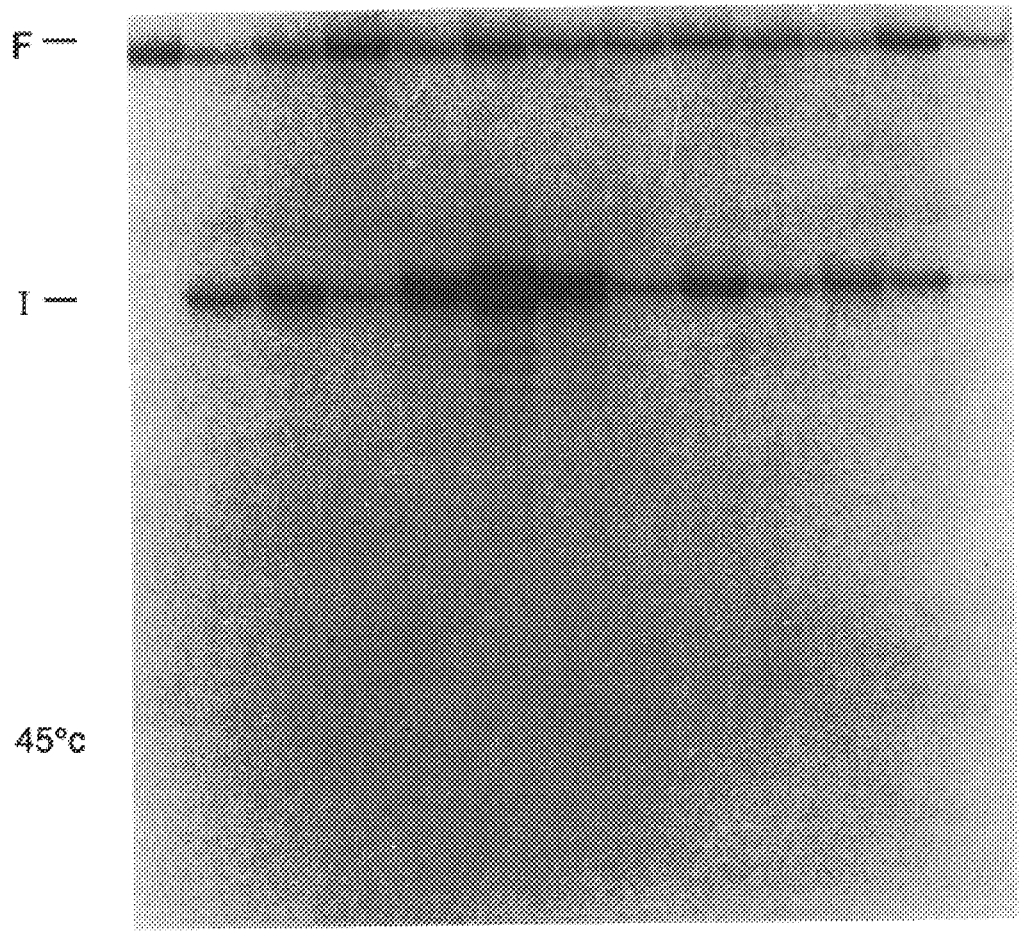
FIG. 7 is an autoradiogram demonstrating the recognition of base substitution mismatches by purified CEL I in the presence of AmpliTaq DNA polymerase. (I) indicates the primary incision site at the phosphodiester bond 3' of a mismatched nucleotide. Panel 7A illustrates cleavage of the substrate in the presence of both CEL I and DNA polymerase. In panel 7B, CEL I was omitted.
Figure 7B:
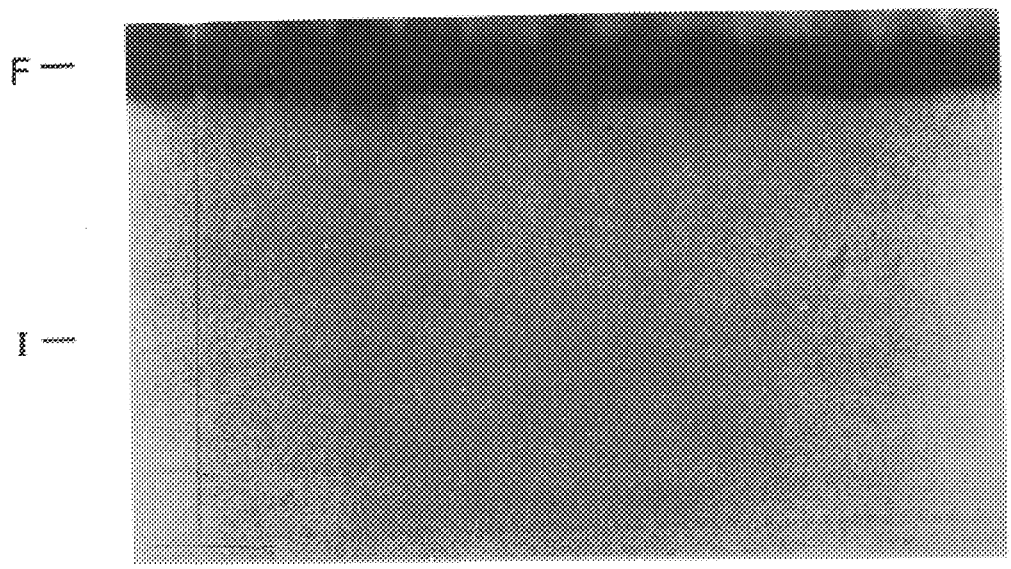

Other combinations of mismatched substrates are also recognized by CEL I and incised on one of the two DNA strands of each DNA duplex. Some of these substrates are less efficiently incised compared with those containing DNA loops; therefore 45° C. was used for incubation instead of 37° C. Substrates with the 5' termini of the top strands labeled were used in this study. The autoradiogram of FIG. 7 shows that mismatches containing a C residue are the preferred mismatch substrates with C/C often better than C/A and C/T. The incisions at these mismatches tend to produce two alternate incision positions, one at the phosphodiester bond 3' of the mismatched C residue, one at the phosphodiester bond one nucleotide further removed in the 3' direction. Whether alternate incision sites will be observed for these mismatches within another DNA sequence context has not been investigated. One possible explanation for this phenomenon may be greater basepair destabilization next to a mismatch that contains a C residue than for other base-substitutions. Alternatively, the specific mismatched nucleotide may shift one position to the 3' side because the next nucleotide is also a C residue and the two residues can exchange their roles in the pairing with the G residue in the opposite DNA strand. For base substitution mismatched basepairs, CEL I specificity in the presence of AmpliTaq DNA polymerase, with respect to the top strand, is C/C≧C/A~C/T≧G/G>A/C~A/A~T/C>T/G~G/T~G/A~A/G>T/T (FIG. 7A). Because eubacterial DNA polymerases are known to incise at unusual DNA structures (8), a test was conducted to determine whether AmpliTaq DNA polymerase by itself will incise at the 13 substrates used in FIG. 7. Under extended exposure of the autoradiogram, no mismatch incision by the AmpliTaq DNA polymerase was observed (FIG. 7B).

EXAMPLE IX

Detection of DNA mutations Using CEL-I and Multiplex Analysis

Figure 8:
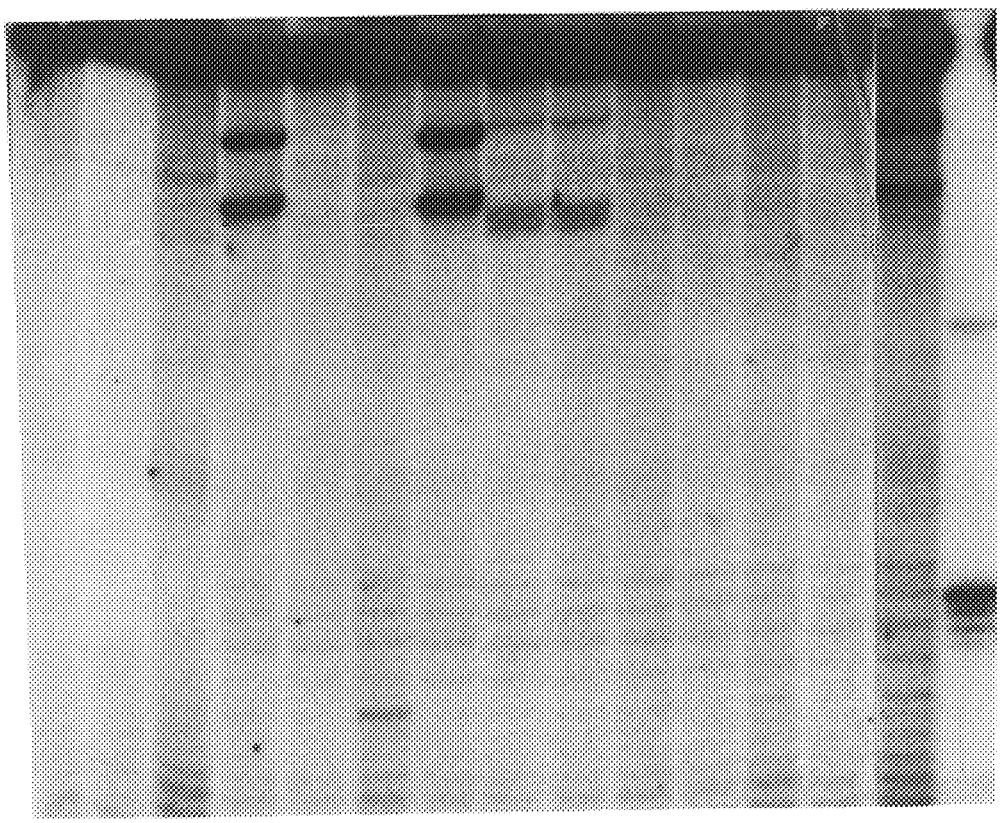
FIG. 8 is an autoradiogram illustrating the ability of CEL I to recognize mutations in pooled DNA samples in the presence of excess wild-type DNA. Lanes 3, 5, 6, 10, 11, 12, and 13 contain single samples containing wild type heteroduplexes. Lanes 4 and 6 contain an AG deletion. Lanes 8 and 9 contain a substrate with an 11 base-pair loop. The samples described above were pooled and treated with CEL I. The results of this "multiplex analysis" are shown in Lane 14.

The sensitivity of CEL I for mismatch detection is illustrated by its ability to detect mutations in pooled DNA samples. DNA was obtained from peripheral blood lymphocytes from individuals undergoing genetic screening at the Fox Chase Cancer Center. Samples were obtained from breast cancer-only, ovarian cancer-only, breast/ovarian cancer syndrome families or from non-breast/ovarian cancer control samples. Unlabeled primers specific for exon 2 of BRCA1 were utilized to PCR amplify this region of the gene. The wild-type PCR products of exon 2 were labeled with gamma $^{32}$P-ATP. Briefly, 10 picomoles of PCR product were purified by the Wizard procedure (Promega). Exon 2 wild-type products were then phosphorylated using T4 kinase and 15 picomoles of gamma $^{32}$P-ATP at 6,000 Ci/mmol in 30 µl 1X kinase buffer (70 mM Tris-HCl (pH 7.6), 10 mM MgCl$_2$, 5 mM dithiothreitol) at 37° C. for 1 hour. The reactions were stopped with 1 µl 0.5M EDTA. The reaction volume was brought up to 50 µl with 1×STE buffer (100 mM NaCl, 20 mM Tris-HCl, pH 7.5, 10 mM EDTA) and processed through a Pharmacia Probe Quant column. Labeled DNA (1 pmol/µl in 100 µl) was then used for hybridization with individual unlabeled PCR amplified experimental samples. For each individual sample, 100 fmol of the unlabeled PCR amplified product was incubated with 200 fmol of the $^{32}$P-labeled wild-type PCR product in CEL I reaction buffer (25 mM KCl, 10 mM MgCl$_2$, 20 mM Tris-HCl, pH 7.5). Following denaturation and renaturation, heteroduplexed, radiolabeled PCR products were exposed to CEL I for 30 minutes at 37° C. in 1X CEL reaction buffer and stopped via the addition of 10 µl stop mix (75% formamide, 47 mM EDTA, 1.5% SDS, xylene cyanol and bromophenol blue). The heteroduplexes were treated with the enzyme individually (lanes 4–13) or pooled in one sample tube (lane 14) and treated. The products of the reaction were loaded onto a 15% polyacrylamide gel containing 7M urea and the results are shown in FIG. 8. Out of the 10 samples analyzed, 2 contained an AG deletion (lanes 4 and 7), 2 contained an 11 base-pair loop (lanes 8 and 9), and the other 6 were wild type (lanes 5, 6, 10, 11, 12, and 13). Cleavage by CEL I at the AG deletion resulted in the formation of two bands, one of approximately 151 nucleotides from the top strand, the other at 112 nucleotides from the bottom strand (lanes 4 and 7). Cleavage by CEL I at 11 base-pair loops resulted in the formation of one band at 147 nucleotides from the top strand, and a group of bands at 109 nucleotides in the bottom strand (lanes 8 and 9). Lanes 1, 2 and 3 contain DNA that was not exposed to CEL I as negative controls, lane 15 contains 64 and 34 bp nucleotide markers. As can be seen in lane 14 of the gel, when the samples were pooled and exposed simultaneously to CEL I, the enzyme cleaved at all of the above listed mutations with no loss of specificity. Also, the PCR products of the wild-type samples showed no non-specific DNA nicking.

Figure 9:
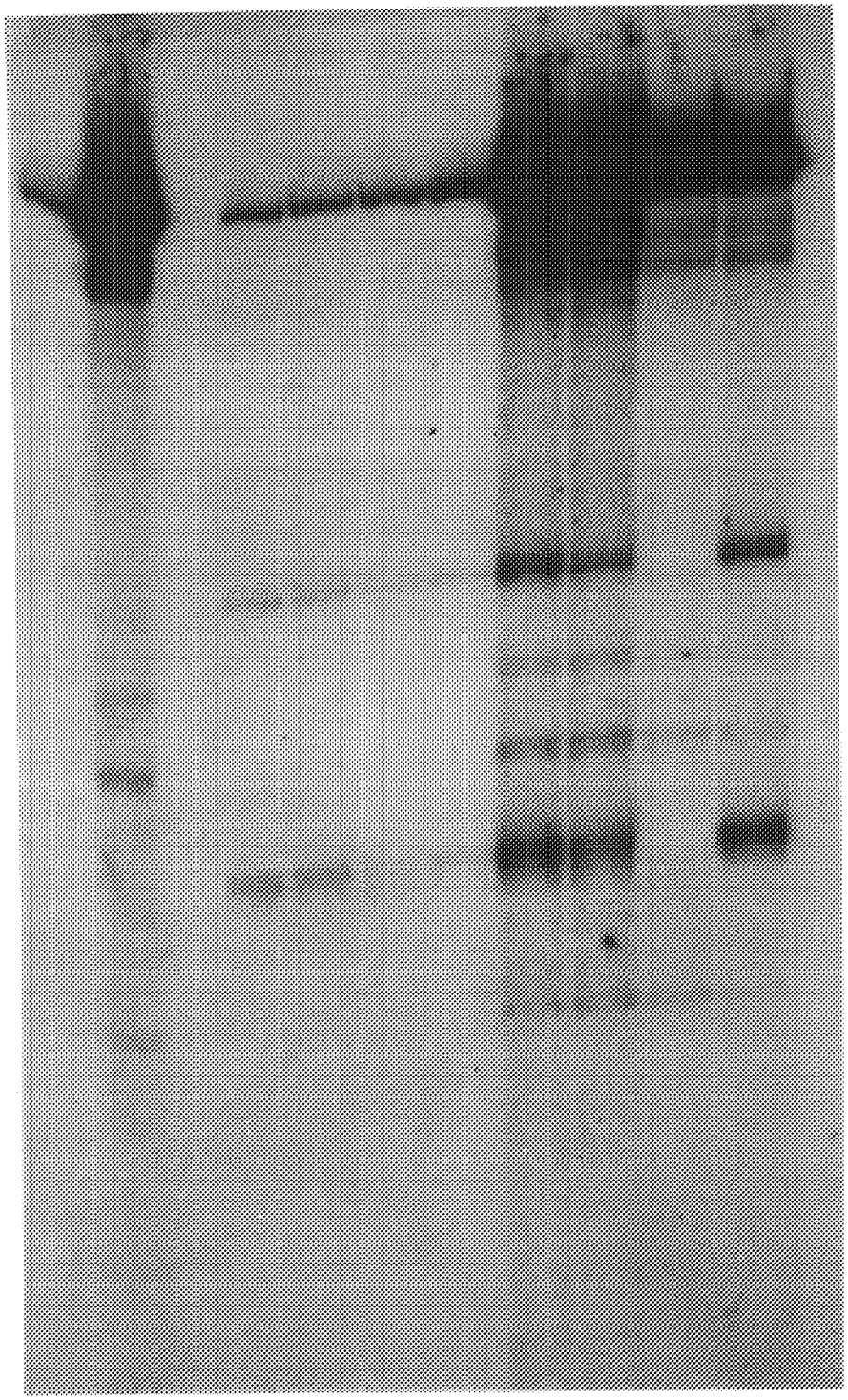
FIG. 9 is an autoradiogram further illustrating the ability of CEL I to recognize mutations in the presence of excess wild-type DNA. 1, 2, 3, 4, 10 or 30 heteroduplexed, radiolabeled PCR products (amplified from exon 2 of the BRCA1 gene) were exposed to CEL I in a single reaction tube and the products run on a 6% polyacrylamide gel. Lanes 1 and 2 are negative controls run in the absence of CEL I. Lane 3 to 11 contain 1 sample with the AG deletion in the presence of increasing amounts of wild-type non-mutated heteroduplexes.

To further illustrate the ability of CEL-I to detect mutations in pooled DNA samples, 1, 2, 3, 5, 10 or 30 heteroduplexed, radiolabelled PCR products, (again amplified from exon 2 of the BRCA1 gene), were exposed to CEL-I in a single reaction tube and the products run on a 6% polyacrylamide gel containing 7M urea. Samples were amplified and radiolabeled as described above. Each pool contained only one sample which had a mutation (AG deletion). The other samples in each pool were wild-type. Lanes 1 and 2 contain control samples which were not exposed to CEL I. In the pooled samples where a mutation was present, CEL-I consistently cleaved the PCR products illustrating the sensitivity of the enzyme in the presence of excess wild-type, non-mutated DNA (Lanes 4, 5, 6, 7, 8, 9, and 11). As a control, heteroduplexed PCR products containing no mutations were analyzed and no cut band corresponding to a mutation appeared (FIG. 9, lanes 3 and 10).

EXAMPLE X

Detection of Mutations and Polymorphisms by CEL-I in Samples Obtained from High Risk Families PCR primer sets specific for the exons in the BRCA1 gene have been synthesized at Fox Chase Cancer Center. The gene sequence of BRCA1 is known. The exon boundaries and corresponding base numbers are shown in table II. Primers to amplify desired sequences can be readily designed by those skilled in the art following the methodology set forth in Current Protocols in Molecular Biology, Ausubel et al., eds, John Wiley and Sons, Inc. (1995). These primers were planned such than in each PCR reaction, one primer is labeled at the 5' termini with a fluorescent-label, 6-FAM, while the other primer is similarly labeled with a label of another color, TET. A PCR product will thus be labeled with two colors such that DNA nicking events in either strand can be observed independently and the measurements corroborated. A summary of the results is presented in Table III.

TABLE II

EXON BOUNDARIES AND CORRESPONDING BASE NUMBERS IN BRCA1

| EXON | BASE #'s |
| --- | --- |
| 1 | 1–100 |
| 2 | 101–199 |
| 3 | 200–253 |
| 5 | 254–331 |
| 6 | 332–420 |
| 7 | 421–560 |
| 8 | 561–665 |
| 9 | 666–712 |
| 10 | 713–788 |
| 11 | 789–4215 |
| 11B | 789–1591 |
| 11C | 1454–2459 |
| 11A | 2248–3290 |
| 11D | 3177–4215 |
| 12 | 4216–4302 |
| 13 | 4303–4476 |
| 14 | 4477–4603 |
| 15 | 4604–4794 |
| 16 | 4795–5105 |
| 17 | 5106–5193 |
| 18 | 5194–5273 |
| 19 | 5274–5310 |
| 20 | 5311–5396 |
| 21 | 5397–5451 |
| 22 | 5452–5526 |
| 23 | 5527–5586 |
| 24 | 5587–5711 |

Figure 10:
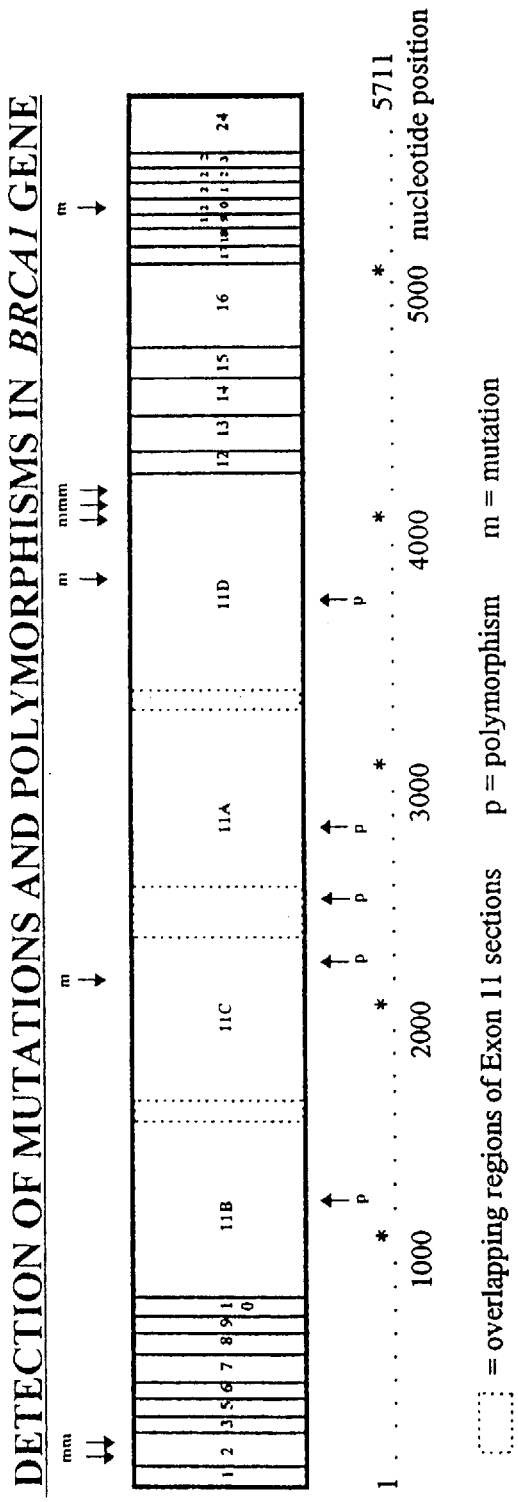
FIG. 10 shows a schematic representative diagram of the BRCA1 gene and the exon boundaries in the gene. The sequence of BRCA1 is set forth as Sequence I.D. No. 1.

FIG. 10 depicts a schematic of the exons present in the BRCA1 gene. Peripheral blood samples from individuals in high risk families were collected and the DNA isolated. The PCR products were amplified using Elongase (BRL) and purified using Wizard PCR Preps (Promega). The DNA was heated to 94° C. and slowly cooled in 1X CEL I buffer (20 mM Tris-HCl pH 7.4, 25 mM KCl, 10 mM MgCl$_2$) to form heteroduplexes. The heteroduplexes were incubated in 20 µl 1X CEL I buffer with 0.2 µl of CEL I and 0.5 units of AmpliTaq at 45° C. for 30 minutes. The reactions were stopped with 1 mM phenanthroline and incubated for an additional 10 minutes at 45° C. The sample was processed through a Centricep column (Princeton Separations) and dried down. One microliter of ABI loading buffer (25 mM EDTA, pH 8.0, 50 mg/ml Blue dextran), 4 µl deionized formamide and 0.5 µl TAMRA internal lane standard were added to the dried DNA pellet. The sample was heated at 90° C. for 2 minutes and then quenched on ice prior to loading. The sample was then loaded onto a 4.25% denaturing 34 cm well-to-read acrylamide gel and analyzed on an ABI 373 Sequencer using GENESCAN 672 software. The 6-FAM labelled primer in this experimental sample was at nucleotide 3177 of the BRCA1 cDNA (region 11D), the TET labelled primer was 73 nucleotides into the intron between exon 11 and exon 12. Each spike represents the presence of a DNA band produced by the cleavage of the heteroduplex by CEL-I where a mutation or a polymorphism is present. One spike represents the size of the CEL I produced fragment from the 3' side of the mismatch site to the 5' 6-FAM label of the top strand. The other spike represents the corresponding fragment in the bottom strand from the 3' side of the mismatch to the 5' TET label. The sum of the two fragments equals one base longer than the length of the PCR product. The 6-FAM panel shows a spike at base #645 from the 6-FAM label and the TET panel shows a spike at base #483 from the TET label, both corresponding to the site of the 5 base deletion at nucleotide 3819 of the BRCA1 cDNA (FIG. 11).

Analysis of exon 11 in another individual was performed using a 6-FAM-labelled primer at nucleotide 1454 of the BRCA1 cDNA (FIG. 12). The TET-labelled primer was at nucleotide 2459 (region 11C). The PCR amplified products were amplified and prepared as described above. In this individual, the 6-FAM panel shows a spike at base #700 and the TET panel shows a spike at #305, each spike corresponding to the site of CEL I incision in the respective DNA strand at a nonsense mutation of A>T at nucleotide 2154 of the BRCA1 cDNA. The 6-FAM panel also shows a spike at base #747 and the TET panel shows a spike at #258 corresponding to the site of a polymorphism C>T at nucleotide 2201 of the BRCA1 cDNA. The nonsense mutation and polymorphism have been confirmed by sequencing of this particular sample (KO-11) using the ABI 377 Sequencer. Spikes that are marked with an asterisk are also present in the no enzyme control lane and represent PCR product background.

Certain individuals have mutations in another region of exon 11, region 11A, on the schematic in FIG. 10. A 6-FAM-labelled primer at nucleotide 2248 of the BRCA1 cDNA and a TET labeled primer at nucleotide 3290 were used to amplify this region of exon 11. Following amplification, the samples were processed as described above. The four 6-FAM panels represent CEL-I reactions with 4 different individual samples. The first panel in FIG. 13A, sample #KO-2, shows one spike at #182 corresponding to the site of a polymorphism T>C at nucleotide 2430 and a second spike at nucleotide #483 corresponding to the site of another polymorphism C>T at nucleotide 2731. The second panel, FIG. 13B, sample #KO-3, shows only the second polymorphism. The third panel, FIG. 13C, sample #KO-7 shows no polymorphism. The fourth panel, FIG. 13D, sample #KO-11, shows two spikes corresponding to the two polymorphisms. It is interesting to note that this sample, KO-11, shows up positive for a nonsense mutation and a polymorphism in the region of exon 11C corresponding to nucleotides 1454–2459 as described above.

TABLE III

SUMMARY OF BRCA1 MUTATIONS
AND POLYMORPHISMS DETECTED BY CEL I

| EXON | NUCLEOTIDE POSITION # | TYPE OF MUTATION |
|---|---|---|
| 2 | 185 | AG deletion |
| 2 | 188 | 11 base deletion |
| 11 C | 2154 | A > T |
| 11 D | 3819 | 5 base deletion |
| 11 D | 4168 | A > G |
| 11 D | 4153 | A deletion |
| 11 D | 4184 | 4 base deletion |
| 20 | 5382 | C insertion |

| EXON | NUCLEOTIDE POSITION # | TYPE OF POLYMORPHISM |
|---|---|---|
| 11 B | 1186 | A > G |
| 11 C | 2201 | T > C |
| 11 A | 2430 | T > C |

TABLE III-continued

SUMMARY OF BRCA1 MUTATIONS
AND POLYMORPHISMS DETECTED BY CEL I

| 11 A | 2731 | C > T |
| 11 D | 3667 | A > G |

Table IV sets forth the 5' and 3' flanking sequences surrounding the mutations detected by CEL I in the present invention. While not exhaustive, it can be seen from the variability of the flanking sequences surrounding these mutations and polymorphisms that CEL I sensitivity and recognition of mismatched DNA heteroduplexes does not appear to be adversely affected by flanking sequences.

TABLE IV

EFFECT OF FLANKING SEQUENCES ON ENDONUCLEASE ACTIVITY OF CEL I

| nucleotide position | EXON | type of change | 5' flanking sequence | 3' flanking sequence |
|---|---|---|---|---|
| 185 | 2 | AG deletion | 5'ATCTT TAGGA3' | 5' AGTGT TCACA 3' |
| 188 | 2 | 11 bp deletion | 5' TTAGA AATCT3' | 5'G the next 4 bp are in intron |
| 1186 | 11 B | A --> G | 5' TAAGC ATTCG 3' | 5' GAAAC CTTG 3' |
| 2154 | 11 C | A --> T | 5' GAGCC CTCGG 3' | 5' AGAAG TCTTC 3' |
| 2201 | 11 C | T --> C | 5' GACAG CTGTC 3' | 5' GATAC CTATG 3' |
| 2430 | 11 A | T --> C | 5' AGTAG TCATC 3' | 5' AGTAT TCATA 3' |
| 2731 | 11 A | C --> T | 5' TGCTC ACGAG 3' | 5' GTTTT CAAAA 3' |
| 3667 | 11 D | A --> G | 5' CAGAA CTCTT 3' | 5' GGAGA CCTCT 3' |
| 3819 | 11 D | 5 bp deletion | 5' GTAAA CATTT 3' | 5' CAATA GTTAT 3' |
| 4153 | 11 D | A deletion | 5' TGATG ACTAC 3' | 5' AGAAA TCTTT 3' |
| 4184 | 11 D | 4 bp deletion | 5' AATAA TTATT 3' | 5' GAAGA CTTCT 3' |
| 4168 | 11 D | A --> G | 5' AACGG TTGCC 3' | 5' CTTGA GAACT 3' |
| 5382 | 20 | C insertion | 5' ATCCC TAGGG 3' | 5' AGGAC TCCTG 3' |

As can be seen from the above described examples, utilization of CEL I has distinct advantages over methods employing other mismatch repair systems during analysis of mutations in the clinical setting. These advantages are summarized in Table V.

TABLE III

Comparison of the advantages of methods employing CEL I over current mismatch detection methods:

| | S1 nuclease method (7) | DNA mismatch glycosylases (8) | MutS binding assay (9) | Chemical cleavage method (10) | T4 endo-nuclease VII (11) | RNase nicking mismatched RNA:DNA (12) | Automated DNA sequencing | ddNTP SSCP finger-printing | Plant mismatch endo-nuclease CEL I |
|---|---|---|---|---|---|---|---|---|---|
| Assay at neutral pH | no | yes | yes | yes | yes | yes | yes | yes | yes |
| Applicable to mutations of unknown positions | yes | no | yes | yes | yes | yes | yes | yes | yes |
| Applicable to all basepair substitutions | unknown | with difficulty | with difficulty | with difficulty | yes | no | yes | yes | yes |
| Applicable to DNA loops, | yes | no | with difficulty | multiple bands | yes | unknown | yes | yes | yes |
| Advantage of single major band in loop detection | no | no | yes | no | yes | no | no | no | yes |
| Advantage of little influence by sequence specificity | no | unknown | yes | unknown | cuts w/o mismatch | unknown | no | with difficulty | yes |
| Advantage of no RNA instability | yes | yes | yes | yes | yes | no | yes | yes | yes |
| Ability to show the position of a detectable mutation | yes | yes | no | yes | yes | yes | yes | with difficulty | yes |
| Ability to tower background with DNA polymerase and DNA ligase recycling reaction | no | no | no | no | with difficulty | no | no | no | yes |
| Advantage to multiplex samples of same color | unknown | no | with difficulty | yes | unknown | no | no | no | yes |
| Advantage to analyze targets of 1 Kbp–3 Kbp | unknown | unknown | with difficulty | yes, up to 1 Kbp | unknown | no | no | no | yes |

REFERENCES

1. Modrich, P. (1994) *Science* 266, 1959–1960.
2. Su, S.-S., Lahue, R. S., Au, K. G., and Moldrich, P. (1988) *J. Biol. Chem.* 263, 5057–5061.
3. Finkelstein, E., Afek U., Gross, E., Aharoni, N., Rosenberg, L., and Halevy, S. (1994) *International Journal of Dermatology* 33, 116–118.
4. Smith, P. K., Krohn, R. I., Hermanson, G. T., Mallia, A. K., Gartner, F. H., Provenzano, M. D., Fujimoto, E. K., Goeke, N. M., Olson, B. J., and Klenk, D. C. (1985) *Analytical Chemistry* 150, 76–85.
5. Gregory D. J., Culp, D. J., and Jahnke, M. R. (1990) *Analytical Biochem.* 185, 324–330.
6. Yeung, A. T., Mattes, W. B., Oh, E. Y., and Grossman, L. (1983) *Proc. Nat. Acad Sci. USA,* 80, 6157–6161.
7. Yeung, A. T., Dinehart, W. J. and Jones, B. K. (1988) *Nucleic Acids Res,* 16, 4539–4554.
8. Lyamichev, V., Brow, M. A. D., and Dahlberg, J. E. (1993) *Science* 260, 778–783.
9. Ramotar, D., Auchincloss, A. H., and Fraser, M. J. (1987) *J. Biol. Chem.* 262, 425–31.
10. Chow, T. Y.-K., and Resnick, M. A. (1987) *J. Biol. Chem.* 262, 17659–17667.
11. Wyen, N. V., Erdei, S., and Farkas, G. L. (1971) *Biochem Biophys. Acta.* 232, 472–83.
12. Brown, P. H., and Ho, D. T. (1987) *Eur. J. Biochem.* 168, 357–364.
13. Hanson, D. M. and Fairley, J. L. (1969) *J. Biol. Chem.* 244, 2440–2449.
14. Nucleases, eds. Linn, S. M., Lloyd, R. S., and Roberts, R. J. Cold Spring Harbor Laboratory Press, 1993.
15. Holloman, W. K., Rowe, T. C., and Rusche, J. R (1981) *J. Biol. Chem.* 256, 5087–5094.
16. Badman, R. (1972) *Genetic Res., Camb.* 20, 213–229.
17. Shank T. E., Rhodes, C. Rigby, P. W. J., and Berg, P. (1975) *Proc. Nat. Acad. Sci. USA,* 72, 989–993.
18. Maekawa, K., Tsunasawa, S., Dibo, G., and Saklyama, F. (1991) *Eur. J. Biochem.* 200, 651–661.
19. Kowalski, D., Kroeker, W. D., and Laskowski, M. Sr. (1976) *Biochemistry* 15, 4457–4462.
20. Kroeker, W. D., Kowalski, D., and Laskowski, M. Sr. (1976) *Biochemistry* 15, 4463–4467.
21. Ardelt, W., and Laskowski, M., Sr. (1971) *Biochem. Biophys. Res., Commun.* 44, 1205–1211.
22. Kowalski, D. (1984) *Nucleic Acids. Res.* 12, 7071–7086.
23. Strickland, J. A., Marzilli L. G., Puckett, Jr., J. M., and Doetsch, P. W. (1991) *Biochemistry* 30, 9749–9756.
24. Doetsch, P. W., McCray, W. H., Lee, K., Bettler, D. R., and Valenzuela, M. R. L. (1988) *Nucleic Acids Res.* 16, 6935–6952.
25. Caren, P. R., Kushner, S. R., and Grossman, L, (1985) *Proc. Nat. Acad. Sci. USA* 82, 4925–4929.
26. Yeh, Y.-C., Liu, H.-F., Ellis, C. A., and Lu, A.-L. (1994) *J. Biol. Chem.* 269, 15498–15504.
27. Welch, W. J., Gerrels, J. I., Thomas, G. P., Lin, J. J.-L., and Feramisco, J. R (1983) *J. Biol. Chem.* 258, 7102–7111.
28. Jackson, S. P., and Tjian, R (1989) *Proc. Nat. Acad. Sci. USA* 86, 1781–1785.
29. Jackson, S. P., and Tjian, R (1988) *Cell* 55, 125–133.
30. He, J., and Furmanski, P. (1995) *Nature* 373, 721–724.
31. Peeples, M. E. (1988) *Virology* 162, 255–259.
32. Buckley, A., and Gould, E. A. (1988) *J. Gen. Virology,* 69, 1913–1920.
33. Gauffre, A., Viron, A., Barel, M., Hermann, J., Puvion, E., and Frade, R. (1992) *Molecular Immunology* 29, 1113–1120.
34. Jones, B. K. and Yeung, A. T. (1988) *Proc. Natl. Acad. Sci. USA* 85, 8410–8414.
35. Sarker, et al., (1992) *Nucleic Acids Research* 20:871–878.
36. Meyers, R. M. et al., (1986) CSHSQB 52:275.

What is claimed is:

1. A method for determining a mutation in a target sequence of a single stranded polynucleotide with reference to a non-mutated sequence of a polynucleotide that is hybridizable with the polynucleotide including said target sequence, wherein said polynucleotides are amplified, labeled with a detectable marker, hybridized to one another, subjected to the activity of an endonuclease and analyzed for the presence of said mutation, the improvement comprising the use of a mismatch endonuclease enzyme of plant origin, the activity of said enzyme comprising:
   a) detection of all mismatches whether known or unknown between said hybridized polynucleotides, said detection occurring over a pH range of 5–9, said enzyme exhibiting substantial activity over the entire pH range;
   b) catalytic formation of a substantially single-stranded nick at a target sequence containing a mismatch; and
   c) recognition of a mutation in a target polynucleotide sequence, said recognition being substantially unaffected by flanking polynucleotide sequences.

2. The method as claimed in claim 1 wherein said endonuclease is from celery.

3. The method as claimed in claim 1 wherein said polynucleotide is DNA.

4. The method as claimed in claim 2 wherein the sequences subjected to said endonuclease activity are further subjected to the activity of a protein, said protein being selected from the group consisting of DNA ligase, DNA polymerase, DNA helicase, 3'-5' DNA Exonuclease, DNA binding proteins that bind to DNA termini or a combination of said proteins, thereby reducing non-specific DNA cleavage.

5. The method as claimed in claim 2 wherein the sequences subjected to said endonuclease activity are further subjected to DNA polymerase activity, so as to reduce non-specific DNA cleavage.

6. The method as claimed in claim 2 wherein target DNA is analyzed in the presence of a multiplicity of pooled samples.

7. The method as claimed in claim 2 wherein said polynucleotide is cDNA.

8. The method as claimed in claim 1, wherein said polynucleotides are analyzed on a DNA sequencing gel thereby identifying the location of the mutation in a target DNA strand relative to DNA sequencing molecular weight markers.

9. The method as claimed in claim 1 wherein said determination is employed as an assay for detection of cancer.

10. The method as claimed in claim 1 wherein said determination is employed as an assay for detection of birth defects.

11. A method for determining a mutation in a target sequence of single stranded polynucleotide with reference to a non-mutated sequence of a polynucleotide that is hybridizable with the polynucleotide including said target sequence, wherein said polynucleotides are amplified, labeled with a detectable marker, hybridized to one another, exposed to endonuclease and analyzed for the presence of said mutation, the improvement comprising the use of a mismatch endonuclease enzyme from celery, the activity of said enzyme comprising:
   a) detection of all mismatches whether known or unknown between said hybridized polynucleotides, said detection occurring over a pH range of 5–9, said enzyme exhibiting substantial activity over the entire pH range;
   b) catalytic formation of a substantially single-stranded nick at a target sequence containing a mismatch;
   c) recognition of a mutation in a target polynucleotide said recognition being substantially unaffected by flanking polynucleotide sequences; and
   d) recognition of polynucleotide loops and insertions between said hybridized polynucleotides.

12. The method as claimed in claim 2 wherein the sequences subjected to said endonuclease activity are further subjected to the activity of a protein, said protein being selected from the group consisting of DNA ligase, DNA polymerase, DNA helicase, 3'-5' DNA Exonuclease, DNA binding proteins that bind to DNA termini or a combination of said proteins, thereby stimulating turnover of said endonuclease.

13. The method as claimed in claim 2 wherein said sequences subjected to said endonuclease activity are further subjected to DNA polymerase activity, thereby stimulating turnover of said endonuclease.

14. A mismatch endonuclease enzyme for determining a mutation in a target sequence of single stranded mammalian polynucleotide with reference to a non-mutated sequence in a polynucleotide that is hybridizable with the polynucleotide including said target sequence, said enzyme being isolated from a plant source and effective to:
   a) detect all mismatches, whether known or unknown between said hybridized polynucleotides, said detection occurring over a pH range of 5–9, said enzyme exhibiting substantial activity over the entire pH range;

b) recognize polynucleotide loops and insertions in said hybridized polynucleotides;

c) catalyze formation of a substantially single-stranded nick at the DNA site containing a mismatch;

d) recognize a mutation in a target polynucleotide sequence, said recognition being substantially unaffected by flanking DNA sequences.

15. An enzyme as claimed in claim 14, wherein said enzyme is CEL I.

16. An enzyme as claimed in claim 14, said enzyme being in substantially pure form.

17. An enzyme as claimed in claim 15, said enzyme being in substantially pure form.

* * * * *

SEQUENCE LISTING ( 1 ) GENERAL INFORMATION:

( i i i ) NUMBER OF SEQUENCES: 13

( 2 ) INFORMATION FOR SEQ ID NO:1:

( i ) SEQUENCE CHARACTERISTICS:
( A ) LENGTH: 5711 base pairs
( B ) TYPE: nucleic acid
( C ) STRANDEDNESS: double
( D ) TOPOLOGY: Not Relevant ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:1:

| | | | | | |
|---|---|---|---|---|---|
| AGCTCGCTGA | GACTTCCTGG | ACCCCGCACC | AGGCTGTGGG | GTTTCTCAGA | TAACTGGGCC | 60 |
| CCTGCGCTCA | GGAGGCCTTC | ACCCTCTGCT | CTGGGTAAAG | TTCATTGGAA | CAGAAAGAAA | 120 |
| TGGATTTATC | TGCTCTTCGC | GTTGAAGAAG | TACAAAATGT | CATTAATGCT | ATGCAGAAAA | 180 |
| TCTTAGAGTG | TCCCATCTGT | CTGGAGTTGA | TCAAGGAACC | TGTCTCCACA | AAGTGTGACC | 240 |
| ACATATTTTG | CAAATTTTGC | ATGCTGAAAC | TTCTCAACCA | GAAGAAGGG | CCTTCACAGT | 300 |
| GTCCTTTATG | TAAGAATGAT | ATAACCAAAA | GGAGCCTACA | AGAAAGTACG | AGATTTAGTC | 360 |
| AACTTGTTGA | AGAGCTATTG | AAAATCATTT | GTGCTTTTCA | GCTTGACACA | GGTTTGGAGT | 420 |
| ATGCAAACAG | CTATAATTTT | GCAAAAAAGG | AAAATAACTC | TCCTGAACAT | CTAAAAGATG | 480 |
| AAGTTTCTAT | CATCCAAAGT | ATGGGCTACA | GAAACCGTGC | CAAAAGACTT | CTACAGAGTG | 540 |
| AACCCGAAAA | TCCTTCCTTG | CAGGAAACCA | GTCTCAGTGT | CCAACTCTCT | AACCTTGGAA | 600 |
| CTGTGAGAAC | TCTGAGGACA | AAGCAGCGGA | TACAACCTCA | AAAGACGTCT | GTCTACATTG | 660 |
| AATTGGGATC | TGATTCTTCT | GAAGATACCG | TTAATAAGGC | AACTTATTGC | AGTGTGGGAG | 720 |
| ATCAAGAATT | GTTACAAATC | ACCCCTCAAG | GAACCAGGGA | TGAAATCAGT | TTGGATTCTG | 780 |
| CAAAAAAGGC | TGCTTGTGAA | TTTTCTGAGA | CGGATGTAAC | AAATACTGAA | CATCATCAAC | 840 |
| CCAGTAATAA | TGATTTGAAC | ACCACTGAGA | AGCGTGCAGC | TGAGAGGCAT | CCAGAAAAGT | 900 |
| ATCAGGGTAG | TTCTGTTTCA | AACTTGCATG | TGGAGCCATG | TGGCACAAAT | ACTCATGCCA | 960 |
| GCTCATTACA | GCATGAGAAC | AGCAGTTTAT | TACTCACTAA | AGACAGAATG | AATGTAGAAA | 1020 |
| AGGCTGAATT | CTGTAATAAA | AGCAAACAGC | CTGGCTTAGC | AAGGAGCCAA | CATAACAGAT | 1080 |
| GGGCTGGAAG | TAAGGAAACA | TGTAATGATA | GGCGGACTCC | CAGCACAGAA | AAAAAGGTAG | 1140 |
| ATCTGAATGC | TGATCCCCTG | TGTGAGAGAA | AAGAATGGAA | TAAGCAGAAA | CTGCCATGCT | 1200 |
| CAGAGAATCC | TAGAGATACT | GAAGATGTTC | CTTGGATAAC | ACTAAATAGC | AGCATTCAGA | 1260 |
| AAGTTAATGA | GTGGTTTTCC | AGAAGTGATG | AACTGTTAGG | TTCTGATGAC | TCACATGATG | 1320 |
| GGGAGTCTGA | ATCAAATGCC | AAAGTAGCTG | ATGTATTGGA | CGTTCTAAAT | GAGGTAGATG | 1380 |
| AATATTCTGG | TTCTTCAGAG | AAAATAGACT | TACTGGCCAG | TGATCCTCAT | GAGGCTTTAA | 1440 |
| TATGTAAAAG | TGAAAGAGTT | CACTCCAAAT | CAGTAGAGAG | TAATATTGAA | GACAAAATAT | 1500 |
| TTGGGAAAAC | CTATCGGAAG | AAGGCAAGCC | TCCCCAACTT | AAGCCATGTA | ACTGAAAATC | 1560 |
| TAATTATAGG | AGCATTTGTT | ACTGAGCCAC | AGATAATACA | AGAGCGTCCC | CTCACAAATA | 1620 |
| AATTAAAGCG | TAAAAGGAGA | CCTACATCAG | GCCTTCATCC | TGAGGATTTT | ATCAAGAAAG | 1680 |

| | | | | | | |
|---|---|---|---|---|---|---|
| CAGATTTGGC | AGTTCAAAAG | ACTCCTGAAA | TGATAAATCA | GGGAACTAAC | CAAACGGAGC | 1740 |
| AGAATGGTCA | AGTGATGAAT | ATTACTAATA | GTGGTCATGA | GAATAAAACA | AAAGGTGATT | 1800 |
| CTATTCAGAA | TGAGAAAAAT | CCTAACCCAA | TAGAATCACT | CGAAAAAGAA | TCTGCTTTCA | 1860 |
| AAACGAAAGC | TGAACCTATA | AGCAGCAGTA | TAAGCAATAT | GGAACTCGAA | TTAAATATCC | 1920 |
| ACAATTCAAA | AGCACCTAAA | AAGAATAGGC | TGAGGAGGAA | GTCTTCTACC | AGGCATATTC | 1980 |
| ATGCGCTTGA | ACTAGTAGTC | AGTAGAAATC | TAAGCCCACC | TAATTGTACT | GAATTGCAAA | 2040 |
| TTGATAGTTG | TTCTAGCAGT | GAAGAGATAA | AGAAAAAAA | GTACAACCAA | ATGCCAGTCA | 2100 |
| GGCACAGCAG | AAACCTACAA | CTCATGGAAG | GTAAAGAACC | TGCAACTGGA | GCCAAGAAGA | 2160 |
| GTAACAAGCC | AAATGAACAG | ACAAGTAAAA | GACATGACAG | CGATACTTTC | CCAGAGCTGA | 2220 |
| AGTTAACAAA | TGCACCTGGT | TCTTTTACTA | AGTGTTCAAA | TACCAGTGAA | CTTAAAGAAT | 2280 |
| TTGTCAATCC | TAGCCTTCCA | AGAGAAGAAA | AGAAGAGAA | ACTAGAAACA | GTTAAAGTGT | 2340 |
| CTAATAATGC | TGAAGACCCC | AAAGATCTCA | TGTTAAGTGG | AGAAAGGGTT | TTGCAAACTG | 2400 |
| AAAGATCTGT | AGAGAGTAGC | AGTATTTCAT | TGGTACCTGG | TACTGATTAT | GGCACTCAGG | 2460 |
| AAAGTATCTC | GTTACTGGAA | GTTAGCACTC | TAGGGAAGGC | AAAAACAGAA | CCAAATAAAT | 2520 |
| GTGTGAGTCA | GTGTGCAGCA | TTTGAAAACC | CCAAGGGACT | AATTCATGGT | TGTTCCAAAG | 2580 |
| ATAATAGAAA | TGACACAGAA | GGCTTTAAGT | ATCCATTGGG | ACATGAAGTT | AACCACAGTC | 2640 |
| GGGAAACAAG | CATAGAAATG | GAAGAAAGTG | AACTTGATGC | TCAGTATTTG | CAGAATACAT | 2700 |
| TCAAGGTTTC | AAAGCGCCAG | TCATTTGCTC | CGTTTTCAAA | TCCAGGAAAT | GCAGAAGAGG | 2760 |
| AATGTGCAAC | ATTCTCTGCC | CACTCTGGGT | CCTTAAAGAA | ACAAAGTCCA | AAAGTCACTT | 2820 |
| TTGAATGTGA | ACAAAAGGAA | GAAAATCAAG | GAAAGAATGA | GTCTAATATC | AAGCCTGTAC | 2880 |
| AGACAGTTAA | TATCACTGCA | GGCTTTCCTG | TGGTTGGTCA | GAAAGATAAG | CCAGTTGATA | 2940 |
| ATGCCAAATG | TAGTATCAAA | GGAGGCTCTA | GGTTTTGTCT | ATCATCTCAG | TTCAGAGGCA | 3000 |
| ACGAAACTGG | ACTCATTACT | CCAAATAAAC | ATGGACTTTT | ACAAAACCCA | TATCGTATAC | 3060 |
| CACCACTTTT | TCCCATCAAG | TCATTTGTTA | AAACTAAATG | TAAGAAAAAT | CTGCTAGAGG | 3120 |
| AAAACTTTGA | GGAACATTCA | ATGTCACCTG | AAAGAGAAAT | GGGAAATGAG | AACATTCCAA | 3180 |
| GTACAGTGAG | CACAATTAGC | CGTAATAACA | TTAGAGAAAA | TGTTTTTAAA | GAAGCCAGCT | 3240 |
| CAAGCAATAT | TAATGAAGTA | GGTTCCAGTA | CTAATGAAGT | GGGCTCCAGT | ATTAATGAAA | 3300 |
| TAGGTTCCAG | TGATGAAAAC | ATTCAAGCAG | AACTAGGTAG | AAACAGAGGG | CCAAAATTGA | 3360 |
| ATGCTATGCT | TAGATTAGGG | GTTTTGCAAC | CTGAGGTCTA | TAAACAAAGT | CTTCCTGGAA | 3420 |
| GTAATTGTAA | GCATCCTGAA | ATAAAAAGC | AAGAATATGA | AGAAGTAGTT | CAGACTGTTA | 3480 |
| ATACAGATTT | CTCTCCATAT | CTGATTTCAG | ATAACTTAGA | ACAGCCTATG | GGAAGTAGTC | 3540 |
| ATGCATCTCA | GGTTTGTTCT | GAGACACCTG | ATGACCTGTT | AGATGATGGT | GAAATAAAGG | 3600 |
| AAGATACTAG | TTTTGCTGAA | AATGACATTA | AGGAAAGTTC | TGCTGTTTTT | AGCAAAAGCG | 3660 |
| TCCAGAAAGG | AGAGCTTAGC | AGGAGTCCTA | GCCCTTTCAC | CCATACACAT | TTGGCTCAGG | 3720 |
| GTTACCGAAG | AGGGGCCAAG | AAATTAGAGT | CCTCAGAAGA | GAACTTATCT | AGTGAGGATG | 3780 |
| AAGAGCTTCC | CTGCTTCCAA | CACTTGTTAT | TTGGTAAAGT | AAACAATATA | CCTTCTCAGT | 3840 |
| CTACTAGGCA | TAGCACCGTT | GCTACCGAGT | GTCTGTCTAA | GAACACAGAG | GAGAATTTAT | 3900 |
| TATCATTGAA | GAATAGCTTA | AATGACTGCA | GTAACCAGGT | AATATTGGCA | AAGGCATCTC | 3960 |
| AGGAACATCA | CCTTAGTGAG | GAAACAAAAT | GTTCTGCTAG | CTTGTTTTCT | TCACAGTGCA | 4020 |
| GTGAATTGGA | AGACTTGACT | GCAAATACAA | ACACCCAGGA | TCCTTTCTTG | ATTGGTTCTT | 4080 |

| | | | | | | |
|---|---|---|---|---|---|---|
| CCAAACAAAT | GAGGCATCAG | TCTGAAAGCC | AGGGAGTTGG | TCTGAGTGAC | AAGGAATTGG | 4140 |
| TTTCAGATGA | TGAAGAAAGA | GGAACGGGCT | TGGAAGAAAA | TAATCAAGAA | GAGCAAAGCA | 4200 |
| TGGATTCAAA | CTTAGGTGAA | GCAGCATCTG | GGTGTGAGAG | TGAAACAAGC | GTCTCTGAAG | 4260 |
| ACTGCTCAGG | GCTATCCTCT | CAGAGTGACA | TTTTAACCAC | TCAGCAGAGG | GATACCATGC | 4320 |
| AACATAACCT | GATAAAGCTC | CAGCAGGAAA | TGGCTGAACT | AGAAGCTGTG | TTAGAACAGC | 4380 |
| ATGGGAGCCA | GCCTTCTAAC | AGCTACCCTT | CCATCATAAG | TGACTCTTCT | GCCCTTGAGG | 4440 |
| ACCTGCGAAA | TCCAGAACAA | AGCACATCAG | AAAAAGCAGT | ATTAACTTCA | CAGAAAGTA | 4500 |
| GTGAATACCC | TATAAGCCAG | AATCCAGAAG | GCCTTTCTGC | TGACAAGTTT | GAGGTGTCTG | 4560 |
| CAGATAGTTC | TACCAGTAAA | AATAAAGAAC | CAGGAGTGGA | AAGGTCATCC | CCTTCTAAAT | 4620 |
| GCCCATCATT | AGATGATAGG | TGGTACATGC | ACAGTTGCTC | TGGGAGTCTT | CAGAATAGAA | 4680 |
| ACTACCCATC | TCAAGAGGAG | CTCATTAAGG | TTGTTGATGT | GGAGGAGCAA | CAGCTGGAAG | 4740 |
| AGTCTGGGCC | ACACGATTTG | ACGGAAACAT | CTTACTTGCC | AAGGCAAGAT | CTAGAGGGAA | 4800 |
| CCCCTTACCT | GGAATCTGGA | ATCAGCCTCT | TCTCTGATGA | CCCTGAATCT | GATCCTTCTG | 4860 |
| AAGACAGAGC | CCCAGAGTCA | GCTCGTGTTG | GCAACATACC | ATCTTCAACC | TCTGCATTGA | 4920 |
| AAGTTCCCCA | ATTGAAAGTT | GCAGAATCTG | CCCAGAGTCC | AGCTGCTGCT | CATACTACTG | 4980 |
| ATACTGCTGG | GTATAATGCA | ATGGAAGAAA | GTGTGAGCAG | GGAGAAGCCA | GAATTGACAG | 5040 |
| CTTCAACAGA | AAGGGTCAAC | AAAAGAATGT | CCATGGTGGT | GTCTGGCCTG | ACCCCAGAAG | 5100 |
| AATTTATGCT | CGTGTACAAG | TTTGCCAGAA | AACACCACAT | CACTTTAACT | AATCTAATTA | 5160 |
| CTGAAGAGAC | TACTCATGTT | GTTATGAAAA | CAGATGCTGA | GTTTGTGTGT | GAACGGACAC | 5220 |
| TGAAATATTT | TCTAGGAATT | GCGGGAGGAA | AATGGGTAGT | TAGCTATTTC | TGGGTGACCC | 5280 |
| AGTCTATTAA | AGAAAGAAAA | ATGCTGAATG | AGCATGATTT | TGAAGTCAGA | GGAGATGTGG | 5340 |
| TCAATGGAAG | AAACCACCAA | GGTCCAAAGC | GAGCAAGAGA | ATCCAGGAC | AGAAAGATCT | 5400 |
| TCAGGGGCT | AGAAATCTGT | TGCTATGGGC | CCTTCACCAA | CATGCCCACA | GATCAACTGG | 5460 |
| AATGGATGGT | ACAGCTGTGT | GGTGCTTCTG | TGGTGAAGGA | GCTTTCATCA | TTCACCCTTG | 5520 |
| GCACAGGTGT | CCACCCAATT | GTGGTTGTGC | AGCCAGATGC | CTGGACAGAG | GACAATGGCT | 5580 |
| TCCATGCAAT | TGGGCAGATG | TGTGAGGCAC | CTGTGGTGAC | CCGAGAGTGG | GTGTTGGACA | 5640 |
| GTGTAGCACT | CTACCAGTGC | CAGGAGCTGG | ACACCTACCT | GATACCCAG | ATCCCCACA | 5700 |
| GCCACTACTG | A | | | | | 5711 |

( 2 ) INFORMATION FOR SEQ ID NO:2:

( i ) SEQUENCE CHARACTERISTICS:
        ( A ) LENGTH: 63 base pairs
        ( B ) TYPE: nucleic acid
        ( C ) STRANDEDNESS: single
        ( D ) TOPOLOGY: Not Relevant ( i i ) MOLECULE TYPE: other nucleic acid
        ( A ) DESCRIPTION: /desc = "Top strand of substrate
            Nos. 1, 12, 13, and 14."

( i i i ) HYPOTHETICAL: NO ( i v ) ANTI-SENSE: NO ( i x ) FEATURE:
        ( A ) NAME/KEY: misc_feature
        ( B ) LOCATION: 1..63
        ( D ) OTHER INFORMATION: /product="Substrate No. 1"
           / standard_name= "top strand 5'to 3'"

( x i ) SEQUENCE DESCRIPTION: SEQ ID NO:2:

```
CCGTCATGCT  AGTTCACTTT  ATGCTTCCGG  CTCGCGTCAT  GTGTGGAATT  GTGATTAAAA        60

TCG                                                                           63
```

( 2 ) INFORMATION FOR SEQ ID NO:3:

( i ) SEQUENCE CHARACTERISTICS:
    ( A ) LENGTH: 63 base pairs
    ( B ) TYPE: nucleic acid
    ( C ) STRANDEDNESS: single
    ( D ) TOPOLOGY: Not Relevant ( i i ) MOLECULE TYPE: other nucleic acid
    ( A ) DESCRIPTION: /desc = "Bottom strand of Substrate
      Nos. 1, 2, 3, 4, 5, 7, 10, 15"

( i i i ) HYPOTHETICAL: NO ( i v ) ANTI-SENSE: NO ( x i ) SEQUENCE DESCRIPTION: SEQ ID NO:3:

```
GCGATTTTAA  TCACAATTCC  ACACATGACG  CGAGCCGGAA  GCATAAAGTG  AACTAGCATG        60

ACG                                                                           63
```

( 2 ) INFORMATION FOR SEQ ID NO:4:

( i ) SEQUENCE CHARACTERISTICS:
    ( A ) LENGTH: 64 base pairs
    ( B ) TYPE: nucleic acid
    ( C ) STRANDEDNESS: single
    ( D ) TOPOLOGY: Not Relevant ( i i ) MOLECULE TYPE: other nucleic acid
    ( A ) DESCRIPTION: /desc = "Top strand of Substrate No.
      2"

( i i i ) HYPOTHETICAL: NO ( i v ) ANTI-SENSE: NO ( x i ) SEQUENCE DESCRIPTION: SEQ ID NO:4:

```
CCGTCATGCT  AGTTCACTTT  ATGCTTCCGG  CTCGGCGTCA  TGTGTGGAAT  TGTGATTAAA        60

ATCG                                                                          64
```

( 2 ) INFORMATION FOR SEQ ID NO:5:

( i ) SEQUENCE CHARACTERISTICS:
    ( A ) LENGTH: 64 base pairs
    ( B ) TYPE: nucleic acid
    ( C ) STRANDEDNESS: single
    ( D ) TOPOLOGY: Not Relevant ( i i ) MOLECULE TYPE: other nucleic acid
    ( A ) DESCRIPTION: /desc = "Top strand of Substrate No.
      3"

( i i i ) HYPOTHETICAL: NO ( i v ) ANTI-SENSE: NO ( x i ) SEQUENCE DESCRIPTION: SEQ ID NO:5:

```
CCGTCATGCT  AGTTCACTTT  ATGCTTCCGG  CTCGTCGTCA  TGTGTGGAAT  TGTGATTAAA        60

ATCG                                                                          64
```

( 2 ) INFORMATION FOR SEQ ID NO:6:

( i ) SEQUENCE CHARACTERISTICS:
    ( A ) LENGTH: 64 base pairs
    ( B ) TYPE: nucleic acid (C) STRANDEDNESS: single
(D) TOPOLOGY: Not Relevant (ii) MOLECULE TYPE: other nucleic acid
(A) DESCRIPTION: /desc = "Top strand of Substrate No. 4."

(iii) HYPOTHETICAL: NO (iv) ANTI-SENSE: NO (xi) SEQUENCE DESCRIPTION: SEQ ID NO:6:

CCGTCATGCT AGTTCACTTT ATGCTTCCGG CTCGACGTCA TGTGTGGAAT TGTGATTAAA 60

ATCG 64

(2) INFORMATION FOR SEQ ID NO:7:

(i) SEQUENCE CHARACTERISTICS:
(A) LENGTH: 64 base pairs
(B) TYPE: nucleic acid
(C) STRANDEDNESS: single
(D) TOPOLOGY: Not Relevant (ii) MOLECULE TYPE: other nucleic acid
(A) DESCRIPTION: /desc = "Top strand of Substrate No. 5."

(iii) HYPOTHETICAL: NO (iv) ANTI-SENSE: NO (xi) SEQUENCE DESCRIPTION: SEQ ID NO:7:

CCGTCATGCT AGTTCACTTT ATGCTTCCGG CTCGCCGTCA TGTGTGGAAT TGTGATTAAA 60

ATCG 64

(2) INFORMATION FOR SEQ ID NO:8:

(i) SEQUENCE CHARACTERISTICS:
(A) LENGTH: 63 base pairs
(B) TYPE: nucleic acid
(C) STRANDEDNESS: single
(D) TOPOLOGY: Not Relevant (ii) MOLECULE TYPE: other nucleic acid
(A) DESCRIPTION: /desc = "Top strand of Substrate Nos. 6, 7, 8, 18."

(iii) HYPOTHETICAL: NO (iv) ANTI-SENSE: NO (xi) SEQUENCE DESCRIPTION: SEQ ID NO:8:

CCGTCATGCT AGTTCACTTT ATGCTTCCGG CTCACGTCAT GTGTGGAATT GTGATTAAAA 60

TCG 63

(2) INFORMATION FOR SEQ ID NO:9:

(i) SEQUENCE CHARACTERISTICS:
(A) LENGTH: 63 base pairs
(B) TYPE: nucleic acid
(C) STRANDEDNESS: single
(D) TOPOLOGY: Not Relevant (ii) MOLECULE TYPE: other nucleic acid
(A) DESCRIPTION: /desc = "Top strand of Substrate Nos. 9, 10, 11, 19."

(iii) HYPOTHETICAL: NO (iv) ANTI-SENSE: NO (xi) SEQUENCE DESCRIPTION: SEQ ID NO:9:

CCGTCATGCT AGTTCACTTT ATGCTTCCGG CTCCCGTCAT GTGTGGAATT GTGATTAAAA 60

TCG 63

(2) INFORMATION FOR SEQ ID NO:10:

(i) SEQUENCE CHARACTERISTICS:
  (A) LENGTH: 63 base pairs
  (B) TYPE: nucleic acid
  (C) STRANDEDNESS: single
  (D) TOPOLOGY: Not Relevant (ii) MOLECULE TYPE: other nucleic acid
  (A) DESCRIPTION: /desc = "Top strand of Substrate Nos. 15, 16, 17, 20."

(iii) HYPOTHETICAL: NO (iv) ANTI-SENSE: NO (xi) SEQUENCE DESCRIPTION: SEQ ID NO:10:

CCGTCATGCT AGTTCACTTT ATGCTTCCGG CTCTCGTCAT GTGTGGAATT GTGATTAAAA 60

TCG 63

(2) INFORMATION FOR SEQ ID NO:11:

(i) SEQUENCE CHARACTERISTICS:
  (A) LENGTH: 63 base pairs
  (B) TYPE: nucleic acid
  (C) STRANDEDNESS: single
  (D) TOPOLOGY: Not Relevant (ii) MOLECULE TYPE: other nucleic acid
  (A) DESCRIPTION: /desc = "Bottom strand of Substrate Nos. 6, 9, 12, 20."

(iii) HYPOTHETICAL: NO (iv) ANTI-SENSE: NO (xi) SEQUENCE DESCRIPTION: SEQ ID NO:11:

GCGATTTTAA TCACAATTCC ACACATCACG AGAGCCGGAA GCATAAAGTG AACTAGCATG 60

ACG 63

(2) INFORMATION FOR SEQ ID NO:12:

(i) SEQUENCE CHARACTERISTICS:
  (A) LENGTH: 63 base pairs
  (B) TYPE: nucleic acid
  (C) STRANDEDNESS: single
  (D) TOPOLOGY: Not Relevant (ii) MOLECULE TYPE: other nucleic acid
  (A) DESCRIPTION: /desc = "Bottom strand of Substrate Nos. 8, 13, 16, 19."

(iii) HYPOTHETICAL: NO (iv) ANTI-SENSE: NO (xi) SEQUENCE DESCRIPTION: SEQ ID NO:12:

GCGATTTTAA TCACAATTCC ACACATCACG GGAGCCGGAA GCATAAAGTG AACTAGCATG 60

ACG 63

(2) INFORMATION FOR SEQ ID NO:13:

(i) SEQUENCE CHARACTERISTICS:
  (A) LENGTH: 63 base pairs

-continued

```
( B ) TYPE: nucleic acid
( C ) STRANDEDNESS: single
( D ) TOPOLOGY: Not Relevant ( i i ) MOLECULE TYPE: other nucleic acid
        ( A ) DESCRIPTION: /desc = "Bottom strand of Substrate
              Nos. 11, 14, 17, 18."

( i i i ) HYPOTHETICAL: NO ( i v ) ANTI-SENSE: NO ( x i ) SEQUENCE DESCRIPTION: SEQ ID NO:13:

GCGATTTTAA  TCACAATTCC  ACACATCACG  TGAGCCGGAA  GCATAAAGTG  AACTAGCATG       60

ACG                                                                         63
```